United States Patent
Kaplan et al.

(10) Patent No.: US 10,106,852 B2
(45) Date of Patent: *Oct. 23, 2018

(54) MUTATED ACVR1 FOR DIAGNOSIS AND TREATMENT OF FIBRODYPLASIA OSSIFICANS PROGRESSIVA (FOP)

(71) Applicant: The Trustees of the University of Pennsylvania, Philadelphia, PA (US)

(72) Inventors: Frederick S. Kaplan, Philidelphia, PA (US); Eileen M. Shore, Fort Washington, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 114 days.

This patent is subject to a terminal disclaimer.

(21) Appl. No.: 14/521,143

(22) Filed: Oct. 22, 2014

(65) Prior Publication Data

US 2015/0203918 A1 Jul. 23, 2015

Related U.S. Application Data

(62) Division of application No. 12/296,275, filed as application No. PCT/US2007/009357 on Apr. 17, 2007, now Pat. No. 8,895,711.

(60) Provisional application No. 60/792,646, filed on Apr. 18, 2006.

(51) Int. Cl.
| | |
|---|---|
| C12Q 1/68 | (2018.01) |
| C12P 19/34 | (2006.01) |
| C07H 21/02 | (2006.01) |
| C07H 21/04 | (2006.01) |
| C12Q 1/6883 | (2018.01) |
| C07K 14/00 | (2006.01) |
| C07K 14/47 | (2006.01) |
| C07K 14/71 | (2006.01) |
| C12N 15/85 | (2006.01) |
| G01N 33/68 | (2006.01) |
| A01K 67/027 | (2006.01) |
| C07K 16/40 | (2006.01) |
| G01N 33/573 | (2006.01) |
| A61K 38/00 | (2006.01) |

(52) U.S. Cl.
CPC ........ *C12Q 1/6883* (2013.01); *A01K 67/0275* (2013.01); *C07K 14/001* (2013.01); *C07K 14/4713* (2013.01); *C07K 14/71* (2013.01); *C07K 16/40* (2013.01); *C12N 15/8509* (2013.01); *G01N 33/573* (2013.01); *G01N 33/6893* (2013.01); *A01K 2207/15* (2013.01); *A01K 2217/00* (2013.01); *A01K 2217/075* (2013.01); *A01K 2227/105* (2013.01); *A01K 2267/0306* (2013.01); *A01K 2267/0331* (2013.01); *A61K 38/00* (2013.01); *C12Q 2600/156* (2013.01); *C12Q 2600/158* (2013.01); *G01N 2333/91205* (2013.01); *G01N 2800/10* (2013.01); *G01N 2800/2842* (2013.01)

(58) Field of Classification Search
CPC ...................... C12Q 1/6883; C12Q 2600/156
See application file for complete search history.

(56) References Cited

U.S. PATENT DOCUMENTS

| | | | |
|---|---|---|---|
| 5,863,738 | A | 1/1999 | Dijke et al. |
| 5,925,517 | A | 7/1999 | Tyagi et al. |
| 6,028,290 | A | 2/2000 | Yasuhara et al. |
| 6,060,240 | A | 5/2000 | Kamb et al. |
| 6,150,107 | A | 11/2000 | Glazer et al. |
| 6,297,016 | B1 | 10/2001 | Egholm et al. |
| 6,316,230 | B1 | 11/2001 | Egholm et al. |
| 6,316,610 | B2 | 11/2001 | Lee et al. |
| 6,709,813 | B1 | 3/2004 | Bergmeyer et al. |
| 8,859,752 | B2 * | 10/2014 | Kaplan ............... A61K 31/713 536/24.5 |
| 2004/0058334 | A1 | 3/2004 | Kaplan et al. |
| 2013/0041017 | A1 | 2/2013 | Kaplan et al. |

FOREIGN PATENT DOCUMENTS

WO  WO 02/43759  6/2002

OTHER PUBLICATIONS

Santangelo, P.J. et al. Nucleic Acids Research, 2004, vol. 32, No. 6, pp. 1-9.*
Wharam et al., "Specific detection of DNA and RNA targets using a novel isothermal nucleic acid amplication assay based on the formation of a three-way hunction structure" Nucleic Acids Res. Jun. 1;29(11):E54-E54.
Aldea et al. "Rapid Detection of Herpes Simplex Virus DNA in Genital Ulcers by Real-Time PCR Using SYBR Green I Dye as the Detection Signal" J. Clin. Microbiol. 40:1060-1062 (2002).
Feldman et al., "Ficrodysplasia Ossificans Progressiva, a heritable disorder of severe heterotopic ossification, maps to human chromosome 4q27-31", Am. J. Hum. Genet. 66:128-135, 2000.
Tan et al., "Molecular Beacons", Current Opinion in Chemical Biology 2004, 8:547-553.

* cited by examiner

*Primary Examiner* — Stephen T Kapushoc
(74) *Attorney, Agent, or Firm* — Mark S. Cohen; Pearl Cohen Zedek Latzer Baratz LLP

(57) ABSTRACT

This invention is directed to mutated Activin A type I receptor proteins (ACVR1) and isolated nucleic acids encoding same. The invention also relates to the use of mutated ACVR1 in the diagnosis and treatment of Fibrodysplasia Ossificans Progressiva (FOP).

23 Claims, 6 Drawing Sheets
Specification includes a Sequence Listing.

A

B

```
ACVR1 FOP mutation  178  STLADLLDHSCTSGSGSGLPFLVQRTVAHQITLLE  212

ACVR1                    STLADLLDHSCTSGSGSGLPFLVQRTVARQITLLE  212
ACVR1B                   KTLQDLVYDLSTSGSGSGLPFLVQRTVARTIVLQE  212
ACVR1C                   KTLKDLIYDVTASGSGSGLPLLVQRTIARTIVLQE  211
ACVRL1                   TMLGDLLDSDCTTGSGSGLPFLVQRTVARQVALVE  199
                         -*--*--*----*-*-*-****--***---*--*  206

BMPR1A                   ESLKDLIDQSQSSGSGSGLPLLVQRTIAKQIQMVR  238
BMPR1B                   ESLRDLIEQSQSSGSGSGLPLLVQRTIAKQIQMVK  208
                         **-*-**-*-*-*****-****-***--*---*

TGFBR1              114  ---------------TGLPLLVQRTIARTIVLQE  132
                                        ***--****-****-*----
```

Figure 6

MUTATED ACVR1 FOR DIAGNOSIS AND TREATMENT OF FIBRODYPLASIA OSSIFICANS PROGRESSIVA (FOP)

CROSS-REFERENCE TO RELATED APPLICATIONS

This application is a Divisional application of U.S. Utility application Ser. No. 12/296,275, filed Jun. 15, 2009, which is a National Phase Application of PCT International Application No. PCT/US07/09357, International Filing Date Apr. 17, 2007, claiming priority of U.S. Provisional Patent Application 60/792,646, filed Apr. 18, 2006, all which are incorporated by reference herein in their entirety.

FIELD OF INVENTION

This invention is directed to mutated Activin A type I receptor proteins (ACVR1) and isolated nucleic acids encoding same. The invention also relates to the use of mutated ACVR1 in the diagnosis and treatment of Fibrodysplasia Ossificans Progressiva (FOP).

BACKGROUND OF THE INVENTION

The formation of bone where it is neither needed nor wanted can lead to devastating consequences. Fibrodysplasia Ossificans Progressiva (FOP, OMIM 135100), also known as Myositis Ossificans Progressiva, is the most severe and disabling disorder of extra-skeletal (heterotopic) ossification in humans. Heterotopic ossification in FOP begins in childhood and can be induced by trauma, or may occur without warning. Bone formation is episodic and progressive, leading to extra-articular ankylosis of all major joints of the axial and appendicular skeleton, rendering movement impossible (FIG. 1a).

The earliest pathological finding in FOP is perivascular lymphocytic infiltration into normal-appearing skeletal muscle, followed by muscle-cell degeneration and highly vascular fibroproliferative soft tissue swelling. The fibroproliferative lesions evolve, through an endochondral process, into mature lamellar bone with marrow elements. Heterotopic ossifications are usually first detected around the spine and proximal extremities, then at multiple other places, which leads to dysfunction of articulations and often premature death.

FOP is a rare condition; the prevalence is ~0.6/1 million live births. Reproductive fitness is low, and most cases appear to arise by spontaneous mutation. There is no effective treatment, and soft-tissue trauma (eg, biopsies, surgical procedures, intramuscular injections, or mandibular blocks for dental procedures) and viral illnesses are likely to induce episodes of rapidly progressive heterotopic ossification, with resultant permanent loss of motion in the affected area. Diagnostic errors with FOP are thought to be common and often associated with inappropriate and harmful diagnostic and therapeutic procedures Therefore, a reliable method is needed for an early diagnosis and treatment methods, thereby providing a foundation for development of treatments not only for FOP, but also for the more common disorders of osteogenesis.

SUMMARY OF THE INVENTION

In one embodiment, the invention provides an isolated nucleic acid encoding a mutated Activin A type I receptor protein (ACVR1), represented by SEQ ID NOs: 21-25 and 27-32 or their combination, wherein the isolated nucleic acid enhances activity of bone morphogenetic protein (BMP) receptor or signaling and is pathognomonic of Fibrodysplasia Ossificans Progressiva (FOP) in a subject.

In another embodiment, the invention provides an oligonucleotide of at least 15 nucleotides capable of specifically hybridizing with a sequence of a nucleic acid encoding the mutated Activin A type I receptor protein (ACVR1), wherein the nucleic acid enhances activity of bone morphogenetic protein (BMP) receptor or its signaling and is pathognomonic of Fibrodysplasia Ossificans Progressiva (FOP) and comprises the sequence as set forth in SEQ ID NOs. 21-25 and 27-32, or combination thereof.

In one embodiment, the invention provides a composition, comprising an antibody, a fragment thereof, or a molecular beacon, wherein said antibody, fragment thereof, or molecular beacon is specifically reactive with a mutated Activin A type I receptor protein (ACVR1), represented by SEQ ID NOs: 21-25 and 27-32 or their combination, or a gene encoding said mutated Activin A type I receptor protein (ACVR1) represented by SEQ ID NOs: 21-25 and 27-32 or their combination.

In another embodiment, the invention provides a method of diagnosing Fibrodysplasia Ossificans Progressiva (FOP) in a subject, comprising: contacting a biological sample from said subject with an antibody, a fragment thereof, or a molecular beacon, said antibody, fragment thereof, or molecular beacon specifically reactive with a nucleic acid sequence encoding a mutated Activin A type I receptor protein (ACVR1) represented by SEQ ID NOs: 21-25 and 27-32 or their combination, or an amino acid sequence of the mutated Activin A type I receptor protein (ACVR1) represented by SEQ ID NOs: 21-25 and 27-32 or their combination; and assaying for the presence of said mutated Activin A type I receptor protein (ACVR1), wherein the presence of the mutated Activin A type I receptor protein (ACVR1) in said sample indicates that said subject has Fibrodysplasia Ossificans Progressiva (FOP).

In one embodiment, the invention provides a method of treating Fibrodysplasia Ossificans Progressiva (FOP) in a subject, comprising the step of administering to said subject a siRNA, polyamides, triple-helix-forming agents, antisense RNA, synthetic peptide nucleic acids (PNAs), agRNA, LNA/DNA copolymers, small molecule chemical compounds, or a combination thereof, specific against a nucleic acid encoding a mutated Activin A type I receptor (ACVR1) represented by SEQ ID NOs: 21-25 and 27-32 or their combination, and a wild-type Activin A type I receptor protein (ACVR1) as set forth in SEQ ID NO. 26.

In another embodiment, the invention provides a method of treating a pathology associated with heterotopic ossification in a subject, comprising the step of administering to said subject an therapeutically effective amount of siRNA, polyamides, triple-helix-forming agents, antisense RNA, synthetic peptide nucleic acids (PNAs), agRNA, LNA/DNA copolymers, small molecule chemical compounds, or a combination thereof, specific against a nucleic acid encoding a mutated Activin A type I receptor (ACVR1) represented by SEQ ID NOs: 21-25 and 27-32 or their combination, whereby the Activin A type I receptor (ACVR1) enhances activity or signaling of bone morphogenetic protein (BMP).

In one embodiment, the invention provides a method of enhancing activity or signaling of bone morphogenetic protein (BMP) in a cell, comprising contacting the cell with an effective amount of a mutated ACVR1 protein represented by SEQ ID NOs: 21-25 and 27-32 or their combination, whereby said protein enhances activity or signaling of bone morphogenetic protein (BMP).

In another embodiment, the invention provides a kit for diagnosing Fibrodysplasia Ossificans Progressiva (FOP) in a subject, comprising: an antibody, a fragment thereof, or a molecular beacon, said antibody, fragment thereof, or molecular beacon specifically reactive with a mutated Activin A type I receptor protein (ACVR1) represented by SEQ ID NOs: 21-25 and 27-32 or their combination, or a gene encoding said mutated Activin A type I receptor protein (ACVR1).

In one embodiment, the invention provides a transgenic mouse whose genome comprises a homozygous disruption of an ACVR1 gene such that said Activin A type I receptor protein (ACVR1) gene does not produce functional Activin A type I receptor protein (ACVR1), wherein the mouse's genome additionally comprises a DNA sequence encoding a mutated Activin A type I receptor protein (ACVR1) represented by SEQ ID NOs: 21-25 and 27-32 or their combination, said mouse showing one or more defects similar to the pathological features of a patient afflicted with heterotopic ossification.

BRIEF DESCRIPTION OF THE DRAWINGS

The invention will be better understood from a reading of the following detailed description taken in conjunction with the drawings in which like reference designators are used to designate like elements, and in which:

FIG. 6 shows amino acid homologies among human ACVR1 family members show conservation of the GS domain in human type I BMP/Activin receptors. Protein sequences were aligned using the Clustal W algorithm. At the position analogous to ACVR1 Arg206, there is an arginine (R) in human type I Activin receptors (ACVR1 (SEQ ID NO: 43), ACVR1B (SEQ ID NO: 44), ACVR1C (SEQ ID NO: 45), ACVRL1 (SEQ ID NO: 46)) and TGFβR1 (SEQ ID NO: 49). Of these receptors, only ACVR1 has been found to mediate BMP signaling. By contrast, two other BMP type I receptors (BMPRIA (SEQ ID NO: 47) and BMPRIB (SEQ ID NO: 48)) have a lysine (K) at the position analogous to ACVR1 Arg206. Like arginine, lysine is a positively charged amino acid and is expected to maintain similar function, however this amino acid difference may contribute to receptor specificity and differences in regulation of downstream signaling.

DETAILED DESCRIPTION OF THE INVENTION

Figure 1:
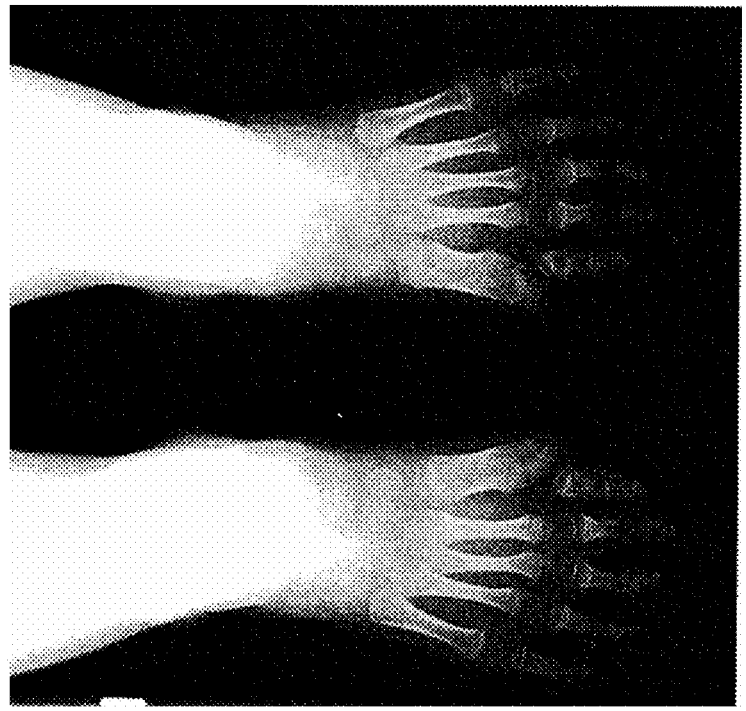
FIG. 1 shows Characteristic clinical features of FOP and linkage mapping in five pedigrees. (a) Extensive heterotopic bone formation typical of FOP is seen by 3-dimensional reconstructed computed tomography (CT) scan of the back of a twelve-year-old child. (b) Anteroposterior radiograph of the feet of a three-year-old child shows symmetrical great toe malformations.
Figure 1:
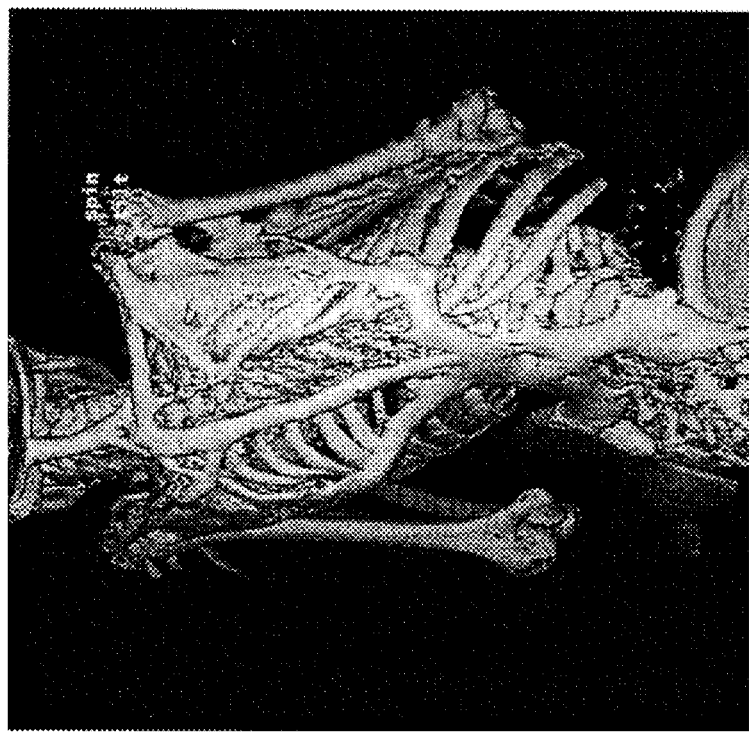

This invention is directed to mutated Activin A type I receptor proteins (ACVR1) and isolated nucleic acids encoding same. The invention also relates to the use of mutated ACVR1 in the diagnosis and treatment of Fibrodysplasia Ossificans Progressiva (FOP).

In another embodiment, the isolated nucleic acid described herein provides a means of substantially increasing bone formation in a subject in need thereof. The contact of the mutated ACVR1 with the appropriate cells, such as mesenchimal stem cells, in one embodiment, creates a cell-scale bone forming mechanism that may be used in other embodiments in pathologies or events requiring rapid or extensive bone formation.

In one embodiment, the mutated nucleic acid is comprised of the nucleic acid sequence encoding ACVR1 Arg206His mutant sequence (R206H; c.617G>A) of:

```
                                          (SEQ ID NO: 21)
MVDGVMILPVLIMIALPSPSMEDEKPKVNPKLYMCVCEGLSCGNEDHCEG

QQCFSSLSINDGFHVYQKGCFQVYEQGKMTCKTPPSPGQAVECCQGDWCN

RNITAQLPTKGKSFPGTQNFHLEVGLIILSVVFAVCLLACLLGVALRKFK

RRNQERLNPRDVEYGTIEGLITTNVGDSTLADLLDHSCTSGSGSGLPFLV

QRTVAHQITLLECVGKGRYGEVWRGSWQGENVAVKIFSSRDEKSWFRETE

LYNTVMLRHENILGFIASDMTSRHSSTQLWLITHYHEMGSLYDYLQLTTL

DTVSCLRIVLSIASGLAHLHIEIFGTQGKPAIAHRDLKSKNILVKKNGQC

CIADLGLAVMHSQSTNQLDVGNNPRVGTKRYMAPEVLDETIQVDCFDSYK

RVDIWAFGLVLWEVARRMVSNGIVEDYKPPFYDVVPNDPSFEDMRKVVCV

DQQRPNIPNRWFSDPTLTSLAKLMKECWYQNPSARLTALRIKKTLTKIDN

SLDKLKTDC
```

In one embodiment, the mutated nucleic acid is comprised of the nucleic acid sequence encoding ACVR1 Gln207Glu mutant sequence (Q207E; c.619C>G) of:

```
                                          (SEQ ID NO. 22)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

AREITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQGKPAIAHRDLKSKNILVKKNGQCCIADLGL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDNSLDKLKTDC
```

In one embodiment, the mutated nucleic acid is comprised of the nucleic acid sequence encoding ACVR1 Gly328Trp mutant sequence (G328W; c.982G>T) of:

```
                                          (SEQ ID NO. 23)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

ARQITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQWKPAIAHRDLKSKNILVKKNGQCCIADLGL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDNSLDKLKTDC
```

In one embodiment, the mutated nucleic acid is comprised of the nucleic acid sequence encoding ACVR1 Gly328Glu mutant sequence (G328E; c.983G>A) of:

```
                                          (SEQ ID NO. 24)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

ARQITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQEKPAIAHRDLKSKNILVKKNGQCCIADLGL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC
```

In one embodiment, the mutated nucleic acid is comprised of the nucleic acid sequence encoding ACVR1 Gly356Asp mutant sequence (G356D; c.1067G>A) of:

```
                                          (SEQ ID NO. 25)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

ARQITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQGKPAIAHRDLKSKNILVKKNGQCCIADLDL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC.
```

In one embodiment, the mutated nucleic acid is comprised of the nucleic acid sequence encoding ACVR1 Ala15Gly mutant sequence (A15G; c.44C>G) of:

```
                                          (SEQ ID NO. 27)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

ARQITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQGKPAIAHRDLKSKNILVKKNGQCCIADLGL
```

-continued

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC.

In one embodiment, the mutated nucleic acid is comprised of the nucleic acid sequence encoding ACVR1 wherein 3 nucleotide deletion replaces Pro197 and Phe 198 with one Leu residue Pro197, Phe198>Leu mutant sequence (P197, F198>L; c.590-592delCTT) of:

(SEQ ID NO. 28)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGL<u>P</u>FLVQRTV

ARQITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQGKPAIAHRDLKSKNILVKKNGQCCIADLGL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC.

In another embodiment, the mutated nucleic acid is comprised of the nucleic acid sequence encoding ACVR1 Gln207Glu mutant sequence (Q207E; c.619C>G) of:

(SEQ ID NO. 29)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

AR<u>EI</u>TLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQGKPAIAHRDLKSKNILVKKNGQCCIADLGL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC.

In another embodiment, the mutated nucleic acid is comprised of the nucleic acid sequence encoding ACVR1 Arg258Ser mutant sequence (R258S; c.744G>C) of:

(SEQ ID NO. 30)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

ARQITLLECVGKGRYGEVWRGSWQGENVAVKIFSSRDEKSWFRETELYNTV

ML<u>R</u>HENILGFIASDMTSRHSSTQLWLITHYHEMGSLYDYLQLTTLDTVSCL

-continued

RIVLSIASGLAHLHIEIFGTQGKPAIAHRDLKSKNILVKKNGQCCIADLGL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC.

In one embodiment, the mutated nucleic acid is comprised of the nucleic acid sequence encoding ACVR1 Gly328Arg mutant sequence (G328R; c.982G>A) of:

(SEQ ID NO. 31)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

ARQITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQ<u>R</u>KPAIAHRDLKSKNILVKKNGQCCIADLGL

AVMHSQSTNQLDVGNNPRVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC.

In one embodiment, the mutated nucleic acid is comprised of the nucleic acid sequence encoding ACVR1 Arg375Pro mutant sequence (R375P; c.1124G>C) of:

(SEQ ID NO. 32)
MVDGVMILPVLIMIALPSPSMEDEKPKVNPKLYMCVCEGLSCGNEDHCEGQ

QCFSSLSINDGFHVYQKGCFQVYEQGKMTCKTPPSPGQAVECCQGDWCNRN

ITAQLPTKGKSFPGTQNFHLEVGLIILSVVFAVCLLACLLGVALRKFKRRN

QERLNPRDVEYGTIEGLITTNVGDSTLADLLDHSCTSGSGSGLPFLVQRTV

ARQITLLECVGKGRYGEVWRGSWQGENVAVKIFSSRDEKSWFRETELYNTV

MLRHENILGFIASDMTSRHSSTQLWLITHYHEMGSLYDYLQLTTLDTVSCL

RIVLSIASGLAHLHIEIFGTQGKPAIAHRDLKSKNILVKKNGQCCIADLGL

AVMHSQSTNQLDVGNN<u>P</u>RVGTKRYMAPEVLDETIQVDCFDSYKRVDIWAFG

LVLWEVARRMVSNGIVEDYKPPFYDVVPNDPSFEDMRKVVCVDQQRPNIPN

RWFSDPTLTSLAKLMKECWYQNPSARLTALRIKKTLTKIDSNLDKLKTDC.

Fibrodysplasia Ossificance Progressiva (FOP) is the most severe and disabling disorder of extra-skeletal (heterotopic) ossification in humans. Heterotopic ossification in FOP begins in childhood and can be induced by trauma in one embodiment, or may occur without warning in another embodiment. In one embodiment, bone formation is episodic, progressive, or extensive, leading to the extra-articular ankylosis of all the major joints of the axial and appendicular skeleton, rendering movement impossible (FIG. 1a). Flareups of FOP arise and progress in one embodiment, in a well-defined spatial pattern that result in ribbons, or sheets, or plates of bone in other embodiment, that fuse the joints of the axial and appendicular skeleton, entombing the patient in a "second skeleton" of heterotopic bone. In one embodiment, one of the more readily recognized skeletal malformations in FOP patients are great toe malformations of metatarsals and proximal phalanges that occurs along with microdactyly, fused interphalangeal joints, and hallux valgus deviations at the metatarsophalangeal joints (FIG. 1b). The severe disability of FOP results in one embodiment, in low reproductive fitness and few examples of inheritance of FOP are known. In one embodiment, death often results by the fifth decade from thoracic insufficiency syndrome. In one embodiment, the methods, compositions and kits described herein are used in treating or providing early diagnosis of FOP in subjects.

In one embodiment, analysis of ACVR1 mRNA expression by RT-PCR and sequencing shows that both mutant and normal mRNAs are expressed in FOP cells, suggesting that the mutation effects are not due to haploinsufficiency, but in one embodiment, are due to altered protein function. In another embodiment, constitutive ACVR1 expression in embryonic chick limbs induced expansion of chondrogenic anlage indicating that ACVR1 signaling alters cell fate and induces undifferentiated mesenchyme to form cartilage. In one embodiment, enhanced ACVR1 activation in FOP results in increased expression of BMP transcriptional targets in FOP cells.

According to this aspect of the invention, and in one embodiment, the invention provides an isolated nucleic acid encoding a mutated Activin A type I receptor protein (ACVR1), wherein the nucleic acid enhances activity of bone morphogenetic protein (BMP) receptor and/or signaling and is pathognomonic of Fibrodysplasia Ossificans Progressiva (FOP).

In another embodiment, the isolated amino acid of the protein has a sequence having at least 82% similarity with any one of the amino acid sequence of SEQ ID NO's 21 to 32 or their combination. In another embodiment the isolated amino acid of the protein has a sequence having at least 85% similarity with any one of the amino acid sequence of SEQ ID NO's 21 to 32 or their combination. In another embodiment the amino acid has a nucleotide sequence having at least 90% similarity with any one of the amino acid sequence of SEQ ID NO's 21 to 32 or their combination. In another embodiment the amino acid has a nucleotide sequence having at least 95% similarity with any one of the amino acid sequence of SEQ ID NO's 21 to 32 or their combination. In another embodiment the amino acid has a nucleotide sequence having 100% similarity with any one of the amino acid sequence of SEQ ID NO's 21 to 32 or their combination. In another embodiment, the isolated nucleic acid used in the invention is encoded by DNA, cDNA, genomic DNA, RNA, or a PCR product.

The invention further encompasses amino acid molecules that differ from any one of the amino acid sequence of SEQ ID NO's 21 to 32 or their combination, due to degeneracy of the genetic code of their encoding gene and thus encode the same mutated Activin A type I receptor protein (ACVR1) as the amino acid sequence shown in any one of the amino acid sequence of SEQ ID NO's 21 to 32 or their combination. It will be appreciated by those skilled in the art that DNA sequence polymorphisms that lead to changes in the amino acid sequences of the mutated Activin A type I receptor protein (ACVR1) may exist within a population (e.g., the human population). Such genetic polymorphism in the gene encoding mutated Activin A type I receptor protein (ACVR1), may exist among individuals within a population due to natural allelic variation. In one embodiment, an allele is one of a group of genes which occur alternatively at a given genetic locus. Such natural allelic variations can typically result in 1-5% variance in the nucleotide sequence of the the gene encoding mutated Activin A type I receptor protein (ACVR1).

Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms in the mutated Activin A type I receptor protein (ACVR1), that are the result of natural allelic variation and that do not alter the functional activity of the mutated Activin A type I receptor protein (ACVR1) are intended to be within the scope of the embodiments described herein. Moreover, nucleic acid molecules encoding the mutated Activin A type I receptor proteins (ACVR1) from other species (the mutated Activin A type I receptor protein (ACVR1) homologues), which have a nucleotide sequence which differs from that of a human Activin A type I receptor protein (ACVR1), are intended to be within the scope of the invention. Nucleic acid molecules corresponding to natural allelic variants and homologues of the the mutated Activin A type I receptor protein (ACVR1) cDNA as described herein, can be isolated based on their identity to the human mutated Activin A type I receptor protein (ACVR1) nucleic acids disclosed herein using human cDNAs, or a portion thereof, as a hybridization probe according to standard hybridization techniques under stringent hybridization conditions. For example, splice variants of human and mouse the mutated Activin A type I receptor protein (ACVR1) cDNA can be isolated based on identity to human and mouse mutated Activin A type I receptor protein (ACVR1).

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. In one embodiment of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the coding or non-coding (or "sense" or "anti-sense") sequence that will encode SEQ ID NO's 21 to 32 or their combination, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In addition to naturally-occurring allelic variants of the mutated Activin A type I receptor protein (ACVR1) sequence that may exist in the population, the skilled artisan will further appreciate that changes can be introduced by mutation into the nucletide sequence encoding mutated Activin A type I receptor protein (ACVR1), thereby leading to changes in the amino acid sequence of the encoded mutated Activin A type I receptor protein (ACVR1), without altering the biological functionality of the encoded mutated Activin A type I receptor protein (ACVR1). Mutations can be introduced by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Activin A type I receptor protein (ACVR1) is preferably replaced with another amino acid residue from the same side chain family. Alternatively, mutations can be introduced randomly along all or part of an Activin A type I receptor protein (ACVR1) coding sequence, such as by saturation mutagenesis, and the resultant mutants can be screened for biological activity of Activin A type I receptor protein (ACVR1), to identify mutants that retain activity, or in another embodiment, the activity of the mutated Activin A type I receptor protein (ACVR1) as described herein. Following mutagenesis, the encoded protein can be expressed recombinantly and the activity of the protein can be determined.

As defined herein an "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

A "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA" is a DNA that has undergone a molecular biological manipulation.

The phrase "nucleic acid encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. In one embodiment, the invention provides recombinant DNA constructs that contain ACVR1 cDNA sequences such as wild type ACVR1 or in another embodiment, recombinant DNA constructs comprising ACVR1 cDNA with the mutations described herein.

Figure 2:
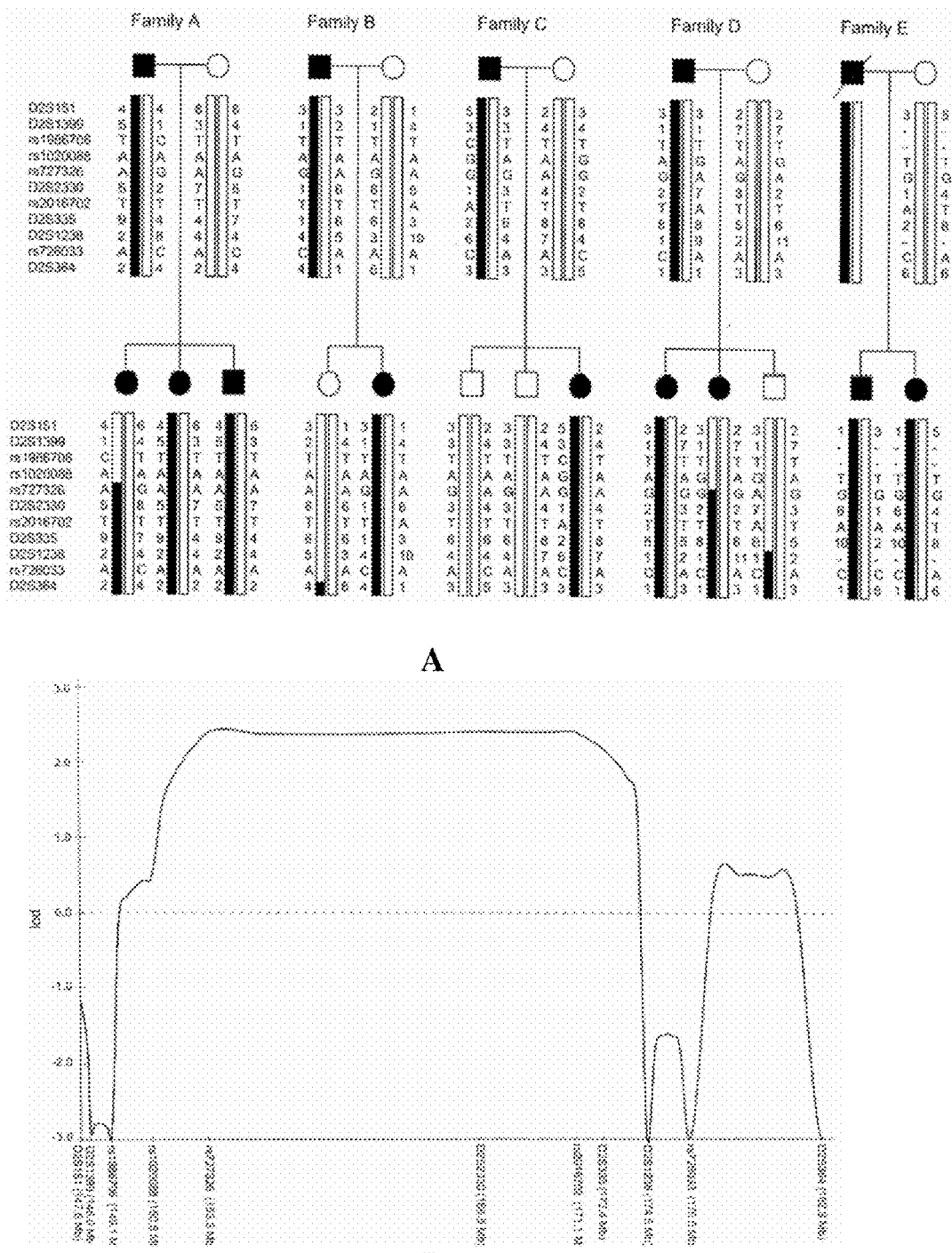
FIG. 2 shows linkage mapping in five pedigrees with classic FOP features. (a) Marker haplotypes on chromosome 2q23-24 that are linked to FOP are indicated by black bars. Microsatellite markers and SNPs are listed at left from centromere to telomere (top to bottom). Haplotypes are interpreted by minimizing recombinants. In each haplotype pair, paternal haplotypes are to the left and maternal to the right. Circles represent females, squares represent males, and filled symbols indicate the presence of FOP. A diagonal line through a symbol indicates that the individual is deceased and unavailable for analysis. (b) Combined multipoint lod plot for markers in the chromosome 2 FOP linkage region. Markers (shown in a) are on the X-axis at approximate relative distances measured in megabases (Mb). Marker positions were obtained from the UCSC GenomeBrowser.

In one embodiment, DNA sequence analysis of all ACVR1 protein-coding exons and splice junctions shows the presence of an identical heterozygous single nucleotide change at cDNA position 617 (c.617G>A) in all examined familial and sporadic FOP patients (FIG. 3b) with classical features of FOP. Investigation of sporadic cases of FOP patients with unambiguous clinical features revealed the presence of the identical de novo mutation in 32 of 32 cases In addition to direct DNA sequence analysis, the G>A nucleotide change can be verified in another embodiment, by differential restriction endonuclease digestion (FIG. 2c). In one embodiment, the mutated ACVR1 used in the methods, compositions and kits described herein comprises the amino acid sequence of SEQ ID NO 21. In another embodiment, the mutated ACVR1 used in the methods, compositions and kits described herein comprises the amino acid sequences of SEQ ID NOs 21-32 or their combination in other embodiments.

In one embodiment, the isolated nucleic acid used in the methods, compositions and kits described herein is one wherein the mutation is a c.44C→G mutation, or one wherein the mutation is a c.590-592delCTT mutation, or one wherein the mutation is a c.744G→C mutation, or one wherein the mutation is a c.982G→A mutation, or one wherein the mutation is a c.1124G→C mutation, or one wherein the mutation is a combination thereof. In another embodiment, the mutation results in A156G mutation. In another embodiment, the mutation results in deletion, which replaces Pro197 and Phe 198 with one Leu residue. In another embodiment, the mutation results in R258S mutation. In another embodiment, the mutation results in G328R mutation. In another embodiment, the mutation results in R375P mutation. In another embodiment, the mutation results in a combination of the mutation described herein.

In one embodiment, the isolated nucleic acid used in the methods, compositions and kits described herein is one wherein the mutation is a c617G→A mutation, or a c619C→G mutation, a c982G→T mutation, a c983G→A mutation, a c1067G→A mutation, or a combination thereof in other embodiments. In one embodiment, the mutation results in a R206H mutation, or a Q207E mutation, a G328W mutation, a G328E mutation, a G356D mutation, or a combination thereof in other embodiment on the encoded Activin A type I receptor protein (ACVR1). In one embodiment, the Activin A type I receptor protein (ACVR1) used in the methods, compositions and kits described herein is encoded from an isolated nucleic acid that is a complication of any one of SEQ ID NO.s 21-32, carrying at least one mutation, or all the mutations, without any other changes to the nucleic acid sequences other than the mutations described herein.

In one embodiment, wild-type ACVR1 protein has the amino acid sequence comprising:

(SEQ ID NO. 26)
MVDGVMILPVLIMIALPSPSMEDEKPKVNPKLYMCVCEGLSCGNEDHCEG

QQCFSSLSINDGFHVYQKGCFQVYEQGKMTCKTPPSPGQAVECCQGDWCN

RNITAQLPTKGKSFPGTQNFHLEVGLIILSVVFAVCLLACLLGVALRKFK

RRNQERLNPRDVEYGTIEGLITTNVGDSTLADLLDHSCTSGSGSGLPFLV

QRTVARQITLLECVGKGRYGEVWRGSWQGENVAVKIFSSRDEKSWFRETE

LYNTVMLRHENILGFIASDMTSRHSSTQLWLITHYHEMGSLYDYLQLTTL

DTVSCLRIVLSIASGLAHLHIEIFGTQGKPAIAHRDLKSKNILVKKNGQC

CIADLGLAVMHSQSTNQLDVGNNPRVGTKRYMAPEVLDETIQVDCFDSYK

RVDIWAFGLVLWEVARRMVSNGIVEDYKPPFYDVVPNDPSFEDMRKVVCV

DQQRPNIPNRWFSDPTLTSLAKLMKECWYQNPSARLTALRIKKTLTKIDN

SLDKLKTDC

Figure 3:
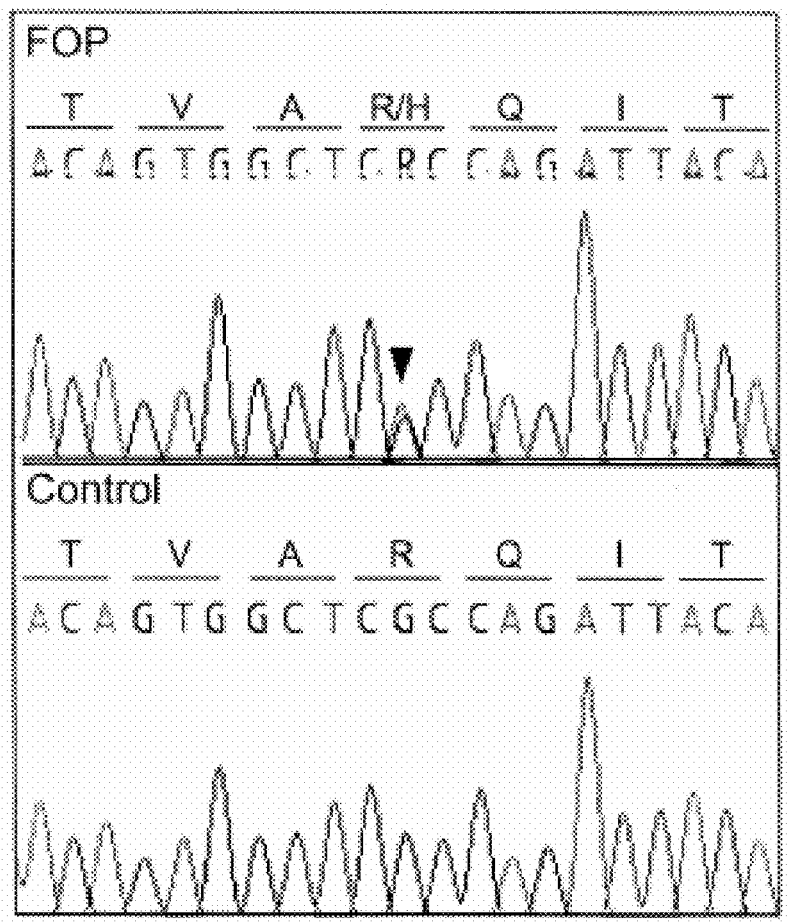
FIG. 3 shows the identification of Arg206His mutations in the ACVR1 gene in patients with FOP. (a) The chromosome 2q FOP critical genomic region spans ~23.9 Mb between markers rs1020088 (centromeric) at 150,654,341 bp and D2S1238 (telomeric) at 174,505,230 bp as annotated by UCSC GenomeBrowser. The ACVR1 gene spans ~138.6 kb of genomic DNA (chromosome 2: 158,418,469-158,557,131). ACVR1 encodes a 509 amino acid protein that contains a ligand binding region, a transmembrane (TM) domain, a glycine-serine (GS) rich domain, and a protein kinase domain. The numbers above the protein representation indicate the amino acids included in each identified domain. The position of the Arg206His mutation in the GS region is indicated by an arrow. The schematics are drawn approximately to scale. (b) Direct DNA sequence analysis of the ACVR1 candidate gene in the chromosome 2q linkage region revealed the identical heterozygous mutation (R206H; at cDNA nucleotide position c.617G>A) in all examined FOP patients. The nucleotide and amino acid sequences are shown for a representative affected individual (top) (SEQ ID NOs: 34 and 33, respectively) and an unaffected control (bottom) (SEQ ID NOs: 36 and 35, respectively). In the nucleotide sequence, R=A or G; in the amino acid sequence R=arginine and H=histidine.

In one embodiment, the ACVR1 c.617G>A mutation causes an amino acid change in codon 206 (R206H; CGC>CAC). In one embodiment, amino acid 206 is highly conserved among vertebrates (FIG. 3b), and is also highly conserved among human ACVR1 family members (FIG. 6). Codon 206 is at the end of the highly conserved glycine/serine (GS) activation domain at the junction of the protein kinase domain (FIG. 3a). Activation of a BMP/TGFβ type I receptor serine-threonine kinase, and consequent signaling, requires phosphorylation at the GS domain by a BMP type II receptor.

Figure 4:
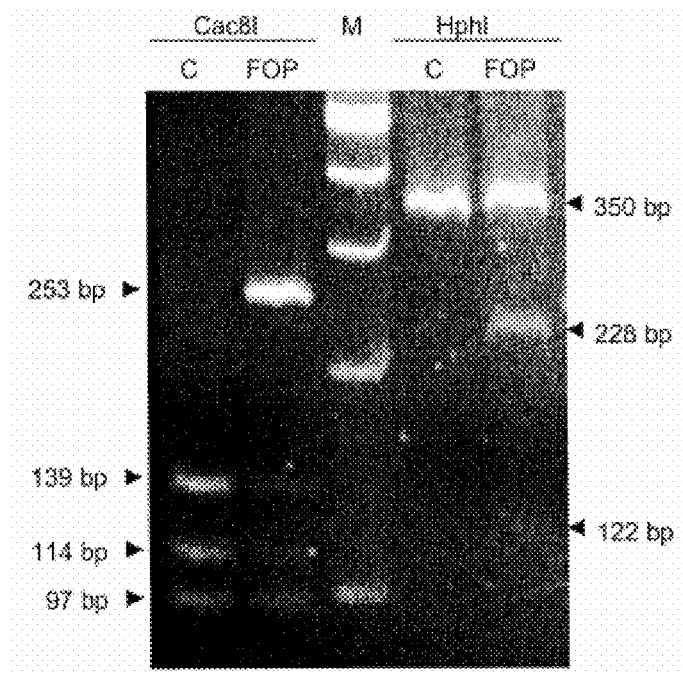
FIG. 4 shows (a) the G>A mutation forms a new HphI site and eliminates a Cac8I site in the mutant allele. PCR product (350 bp) from control DNA (C) is undigested by HphI; the heterozygous mutation in patient DNA results in the undigested product from the normal allele and HphI-digested products (228 and 122 bp) from the mutant allele (FOP). The same PCR product from control DNA is digested by Cac8I to produce three bands (139, 114, and 97 bp) while the mutant allele produces two bands (253 and 97 bp). (b) ACVR1 codon 206 is highly conserved among species. The Arg206His FOP mutation (SEQ ID NO: 37) in the ACVR1 gene (also known as Alk2) occurs within the highly conserved GS domain (amino acids 178-208 in mammals; SEQ ID NOs: 38-41). An * below the sequence indicates an identical amino acid at the corresponding position of ACVR1/ALK2 protein in various species. Clustal W was used for multiple protein sequence alignment.

In one embodiment, PredictProtein and CPHmodels both predict a partial destabilization of the α-helix formed by ACVR1 amino acids 198-206 (FIG. 4). The R206H mutation forms a shorter side chain that alters the electrostatic potential compared to the wild type ACVR1 protein (SEQ ID NO. 26), disrupting intramolecular interactions that stabilize the ACVR1 protein in one embodiment, or altering interactions between the GS domain and other signaling pathway molecules in another embodiment.

In another embodiment, the GS domain is a critical site for binding and activation of R-Smad signaling proteins and is a binding site of FKBP12, an inhibitory protein that prevents leaky activation of the type I receptor in the absence of ligand. In one embodiment, FKBP12 interactions with the GS domain are altered, leading to promiscuous activity of ACVR1. In one embodiment R206H mutations in ACVR1 specifically perturb BMP signaling in FOP involves dysregulation of BMP receptor oligomerization, or internalization, and/or activation of downstream signaling in other embodiments.

In one embodiment, the isolated nucleic acid described herein, which is used in the compositions, methods and kits described herein, is DNA, or RNA, cDNA, genomic DNA, or a PCR product or their combination in other embodiments. In one embodiment, the DNA, or RNA, cDNA, genomic DNA, or a PCR product or their combination as described herein, are detectibly labeled. In another embodiment, the DNA, or RNA, cDNA, genomic DNA, or a PCR product or their combination as described herein, are detectibly labeled with a label that is a radioactive label, or colorimetric, luminescent, fluorescent marker, or gold label in other embodiments.

In one embodiment, the isolated nucleic and amino acids described hereinabove are capable of being hybridized to by the oligonucleotides described herein, wherein the hybridized oligonucleotides are used in the compositions, methods and kits described herein. In one embodiment, the described herein is an oligonucleotide capable of hybridizing to any embodiment of a nucleotide described hereinabove.

In one embodiment, the invention provides an oligonucleotide of at least 15 nucleotides capable of specifically hybridizing with a sequence of the nucleic acid which encodes the mutated Activin A type I receptor protein (ACVR1), wherein the nucleic acid enhances activity of bone morphogenetic protein (BMP) receptor in one embodiment or bone morphogenetic protein (BMP) receptor signaling in another embodiment; and is pathognomonic of Fibrodysplasia Ossificans Progressiva (FOP) and comprises the sequence as set forth in SEQ ID NOs. 21-25 or variants thereof.

In one embodiment, the oligonucleotides described herein, which are capable of specifically hybridizing with a sequence of the nucleic acid which encodes the mutated Activin A type I receptor protein (ACVR1), as described herein, that is used in the compositions, methods and kits described herein, is DNA, or RNA, cDNA, genomic DNA, or a PCR product or their combination in other embodiments. In one embodiment, the DNA, or RNA, cDNA, genomic DNA, or a PCR product or their combination as described herein, are detectibly labeled. In another embodiment, the DNA, or RNA, cDNA, genomic DNA, or a PCR product or their combination as described herein, are detectibly labeled with a label that is a radioactive label, or colorimetric, luminescent, fluorescent marker, or gold label in other embodiments.

In one embodiment, provided herein is a nucleic acid having a sequence complementary to the sequence of the isolated nucleic acid encoding a mutated Activin A type I receptor protein (ACVR1), wherein the nucleic acid enhances activity of bone morphogenetic protein (BMP) receptor and/or signaling and is pathognomonic of Fibrodysplasia Ossificans Progressiva (FOP).

In one embodiment, the isolated nucleic or amino acid sequences described hereinabove, are used in the compositions described herein. In another embodiment, the invention provides a composition, comprising an antibody, or a fragment thereof, or a molecular beacon, in other embodiments, wherein said antibody, fragment thereof, or molecular beacon specifically reactive with a mutated Activin A type I receptor protein (ACVR1), or a gene encoding said mutated Activin A type I receptor protein (ACVR1).

Antibodies of the invention bind selectively to mutated Activin A type I receptor protein (ACVR1) wherein the mutated Activin A type I receptor protein (ACVR1) comprises SEQ IDs NOs 21 to 25 or a combination thereof. In one embodiment, the term "antibody" include complete antibodies (e.g., bivalent IgG, pentavalent IgM) or fragments of antibodies in other embodiments, which contain an antigen binding site. Such fragment include in one embodiment Fab, F(ab')$_2$, Fv and single chain Fv (scFv) fragments. In one embodiment, such fragments may or may not include antibody constant domains. In another embodiment, Fab's lack constant domains which are required for complement fixation. scFvs are composed of an antibody variable light chain ($V_L$) linked to a variable heavy chain ($V_H$) by a flexible linker. scFvs are able to bind antigen and can be rapidly produced in bacteria. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$-$C_{H1}$ and $V_L$-$C_L$) comprise an Fab. Complete antibodies are obtained in one embodiment, from such a library by replacing missing constant domains once a desired $V_H$-$V_L$ combination has been identified.

Antibodies of the invention can be monoclonal antibodies (Mab) in one embodiment, or polyclonal antibodies in another embodiment. Antibodies of the invention which are useful for the compositions, methods and kits of the invention can be from any source, and in addition may be chimeric. In one embodiment, sources of antibodies can be from a mouse, or a rat, or a human in other embodiments. Antibodies of the invention which are useful for the compositions, methods and kits of the invention have reduced antigenicity in humans, and in another embodiment, are not antigenic in humans. Chimeric antibodies for use in the compositions, methods and kits of the invention contain in one embodiment, human amino acid sequences and include humanized antibodies which are non-human antibodies substituted with sequences of human origin to reduce or eliminate immunogenicity, but which retain the binding characteristics of the non-human antibody.

In one embodiment, the compositions, methods and kits of the invention comprise molecular beacons wherein said molecular beacon comprises: an oligonucleotide comprising a stem and a loop structure and having a photoluminescent dye at one of the 5' or 3' ends and a quenching agent at the opposite 3' or 5' ends, wherein said loop consists of about 7-25 bases specifically reactive with a gene sequence encoding said mutated Activin A type I receptor protein (ACVR1).

Molecular beacons were introduced in the mid-1990's as novel probes that can fluorescently detect in solution or in living cells nucleic acid synthesis, expression or trafficking. The basic structure of molecular beacons includes a stem-loop structure with a fluorophore and a quencher at the respective 5' and 3' ends of the molecule. Proximity of the fluorophore to the quencher results in fluorescence resonance energy transfer and quenching of the fluorescence. Upon hybridization of the loop region to a target DNA or RNA in solution or in living cells, the fluorophore and quencher become spatially separated resulting in emission of fluorescence. Molecular beacons have been widely used to detect either DNA or RNA in the real-time quantitative PCR methodologies.

Molecular Beacons comprise in one embodiment, nucleic acid molecules having a target complementary sequence, an affinity pair (or nucleic acid arms) holding the probe in a closed conformation in the absence of a target nucleic acid sequence, and a label pair that interacts when the probe is in a closed conformation. In another embodiment, hybridization of the target nucleic acid and the target complementary sequence separates the members of the affinity pair, thereby shifting the probe to an open conformation. The shift to the open conformation is detectable in one embodiment due to reduced interaction of the label pair, which may be, in one embodiment, a fluorophore and a quencher (e.g., DABCYL and EDANS). Molecular Beacons are fully described in U.S. Pat. No. 5,925,517, the disclosure of which is hereby incorporated by reference.

According to this aspect of the invention and in one embodiment, the invention provides molecular beacon comprising: an oligonucleotide comprising a stem and a loop structure and having a photoluminescent dye at one of the 5' or 3' ends and a quenching agent at the opposite 3' or 5' ends, wherein said loop consists of about 8-25 bases, substantially complimentary to the nucleotide sequence encoding SEQ ID NOs 21-32 or their combination. in another embodiment, the invention provides molecular beacon comprising: an oligonucleotide comprising a stem and a loop structure and having a photoluminescent dye at one of the 5' or 3' ends and a quenching agent at the opposite 3' or 5' ends, wherein said loop consists of about 8-25 bases, substantially complimentary to a nucleotide sequence comprising a combination of any mutation described herein. In another embodiment, the mutated Activin A type I receptor protein (ACVR1) has a R206H mutation, a Q207E mutation, a G328W mutation, a G328E mutation, a G356D mutation, or a combination thereof.

In one embodiment, the molecular beacon of the invention comprises a detectible label in the 5' or 3' ends of the stem. The term "detectable label" refers in one embodiment to a composition or moiety that is detectable by spectroscopic, photochemical, biochemical, immunochemical, electromagnetic, radiochemical (using technetium-99m ($^{99m}$Tc) e.g.), or chemical means such as fluorescence, chemifluoresence, or chemiluminescence, or any other appropriate means. In another embodiment, detectable labels are fluorescent dye molecules, or fluorophores, such fluorescein, phycoerythrin, CY3, CY5, allophycocyanine, Texas Red, peridenin chlorophyll, cyanine, FAM, JOE, TAMRA, TET, VIC. Methods and compositions for detectably labeling molecules, such as oligonucleotides, DNA-DNA hybrids, etc. are well known in the art. See, e.g., U.S. Pat. Nos. 6,316,230; 6,297,016; 6,316,610; 6,060,240; 6,150,107; and 6,028,290, each of which are hereby incorporated by reference in their entirety.

In one embodiment, the photoluminescent dye used in the beacons, methods and kits of the invention is fluorescein, phycoerythrin, CY3, CY5, allophycocyanine, Texas Red, peridenin chlorophyll, cyanine, FAM, JOE, TAMRA, TET, VIC, or a combination thereof. In another embodiment, the FAM is 6-carboxyfluorescein (6-FAM).

In one embodiment, molecular beacon probes according to the present invention utilize any photoluminescent moiety as a detectable moiety. Typically these are dyes. In another embodiment these are fluorescent dyes. Photoluminescence is any process in which a material is excited by radiation such as light in one embodiment, is raised to an excited electronic or vibronic state, and subsequently re-emits that excitation energy as a photon of light. Such processes include in one embodiment fluorescence, which denotes emission accompanying descent from an excited state with paired electrons (a "singlet" state) or unpaired electrons (a "triplet" state) to a lower state with the same multiplicity, i.e., a quantum-mechanically "allowed" transition. Photoluminescence includes in another embodiment phosphorescence which denotes emission accompanying descent from an excited triplet or singlet state to a lower state of different multiplicity, i.e., a quantum mechanically "forbidden" transition. Compared to "allowed" transitions, "forbidden" transitions are associated with relatively longer excited state lifetimes.

In one embodiment, the molecular beacon of the invention, which is used in the methods and kits of the invention, comprises a quencher moiety of a detectable label disposed on the opposing end of the detectible label. In another embodiment, "quencher moiety" as used herein means a molecule that, in close proximity to a donor fluorophore, takes up emission energy generated by the donor and either dissipates the energy as heat or emits light of a longer wavelength than the emission wavelength of the donor. In one embodiment, the quencher is considered to be an acceptor fluorophore. The quenching moiety can act in another embodiment, via proximal (i.e. collisional) quenching or by Forster or fluorescence resonance energy transfer ("FRET") in other embodiments. Quenching by FRET is used in one embodiment when TaqMan™ probes are used while in another embodiment, proximal quenching is used in molecular beacon and scorpion type probes.

In one embodiment, the molecular beacon used in the invention utilize proximal quenching. In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on $R^{-6}$, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from increased distance between the donor and the quencher (acceptor fluorophore). TaqMan® probes (Heid et al., 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). See Tyagi et al., Nature Biotechnology 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

In one embodiment, the compositions, kits and methods of the invention use binary molecular beacons. In another embodiment, since molecular beacons generate a detectable background fluorescence it is beneficial to validate that fluorescence signals are the result of hybridization of the molecular beacon to the target sequence rather than merely the presence of the probe in the sample. In on embodiment, two different molecular beacons with the same loop specificity, each possessing a differently colored fluorophore, are designed to bind to the same target at nearly adjacent positions so that, on hybridization, their fluorophores interact via FRET as described herein. In another embodiment, since the efficiency of FRET is inversely proportional to the distance between the fluorophores, molecular beacons that are bound nonspecifically to the target sequence, fluoresce in their own characteristic emission wavelength but do not to participate in the generation of a FRET signal. In one embodiment, the donor fluorophore (TMR e.g.) is placed at the 5' end of one molecular beacon of the invention and the acceptor fluorophore (Texas red) at the 3' end of the other molecular beacon of the invention, to maximize the efficiency of target-mediated FRET. The fluorophore-bearing arms, or stems of these molecular beacons (as well as the loop sequences) were designed to be complementary to their target sequences. In one embodiment, the sequences of the two probes are chosen so that, when they both bind to the same target sequence, their fluorophores are separated from each other by such number of intervening target nucleotides, so that the intensity of the FRET signal is at a maximum, optimally balancing the negative effect of mutual fluorescence quenching and the positive effect of resonance energy transfer for these particular fluorophores. In one embodiment, the kits of the invention comprise binary molecular beacon system.

Suitable donor fluorophores for use in the molecular beacons, kits and methods of the invention include 6-carboxyfluorescein (6FAM), tetrachloro-6-carboxyfluorescein (TET), 2'-chloro-7'-phenyl-1,4-dichloro-6-carboxyfluorescein (VIC), and the like. Suitable quenchers include tetramethylcarboxyrhodamine (TAMRA) 4-(4-dimethylaminophenylazo)benzoic acid ("DAB CYL" or a DABCYL analog) and the like. Tetramethylrhodamine (TMR) or 5-carboxyrhodamine 6G (RHD) may be combined as donor fluorophores with DABCYL as quencher. Probes for detecting amplified sequence in real time may be stored frozen (−10. to −30° C.) as 100 M stocks. TaqMan MGB probes are available from Applied BioSystems (4316032).

Examples of donor/acceptor label pairs that may be used in connection with the invention, include in one embodiment fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2, 6-FAM/BHQ1 and fluorescein/QSY7 dye. A person holding an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL in one embodiment, and the QSY 7 dyes in other embodiments, advantageously eliminate the potential problem of background fluorescence resulting from direct (i.e., non-sensitized) acceptor excitation. In one embodiment, fluorophore moieties that can be used as one member of a donor-acceptor pair include fluorescein, ROX, and the CY dyes (such as CY5). In another embodiment, quencher moieties that can be used as another member of a donor-acceptor pair include DABCYL and the BLACK HOLE QUENCHER moieties which are available from Biosearch Technologies, Inc., (Novato, Calif.).

In one embodiment, the invention provides a composition, comprising an antibody, a fragment thereof, or a molecular beacon, the antibody, fragment thereof, or molecular beacon specifically reactive with a mutated Activin A type I receptor protein (ACVR1) and wherein the composition in addition comprises another component, which is an antibody, a fragment thereof, or a molecular beacon, that are specifically reactive with a protein or an encoding gene thereof, as listed in Table 1. In another embodiment, the antibody, fragment thereof, or molecular beacon is specifically reactive with nucleic acid coding sequence of SEQ ID NOs: 21-25, or their combination sequence.

In one embodiment, the kits and methods of the invention use molecular beacons labeled with colloidal quantum dots. Colloidal quantum dots (QDs) refer in one embodiment to semiconductor nanocrystals whose photoluminescence emission wavelength is proportional to the size of the crystal. The emission spectra of QDs are narrow, which allows multiwavelength labeling with different sizes of QDs with little overlap. QDs outer surfaces is readily conjugated in another embodiment to the molecular beacons of the invention, resulting in a spectrum of labels that are all excited with a single wavelength. In another embodiment, the QDs used in the invention are CdSe nanocrystals.

In one embodiment QDs of different size are used to label the molecular beacons specific for the genes or nucleotides of Table 1, such that an emmission fingerprint emerges, which will identify the presence of any combination of the nucleotides present in the sample. In one embodiment, the obtained sample emmission is compared with a standard fingerprint of a sample taken from a subject with FOP. In another embodiment, emmission spectra library of inherited FOP or sporadic FOP—specific molecular beacons of the invention labeled with the QDs of the invention is used to determine the molecular beacon cocktail necessary to diagnose or differentiate a given FOP subtype. In one embodiment, the kits of the invention comprise specific cocktail of molecular beacons.

In one embodiment, the antibody, a fragment thereof, or a molecular beacon exhibit substantial complimentarity to their target sequence, which may be a protein, such as mutated ACVR1 protein, or gene encoding the mutated protein and the nucleotides as described in Table 1 on other embodiments. In another embodiment, "complementary" indicates that the oligonucleotide or oligopeptide have a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the antibody, a fragment thereof, or a molecular beacon are sufficiently complimentary to their target sequence, which may be a protein, such as mutated ACVR1 protein, or gene encoding the mutated protein and the nucleotides as described in Table 1 in other embodiments. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, the embodiments of isolated nucleic acids and their encoded amino acid, or the embodiments of compositions described hereinabove or their combination, are used in the methods and kits described herein.

In one embodiment, the invention provides a method of diagnosing Fibrodysplasia Ossificans Progressiva (FOP) in a subject, comprising: contacting a biological sample from said subject with an antibody, a fragment thereof, or a molecular beacon, said antibody, fragment thereof, or molecular beacon specifically reactive with a nucleic acid sequence encoding a mutated Activin A type I receptor protein (ACVR1), or an amino acid sequence of the mutated Activin A type I receptor protein (ACVR1); and assaying for the presence of said mutated Activin A type I receptor protein (ACVR1), wherein the presence of the mutated Activin A type I receptor protein (ACVR1) in said sample indicates that said subject has Fibrodysplasia Ossificans Progressiva (FOP).

In another embodiment, contacting the sample with the compositions and kits of the invention, comprises amplifying the target gene encoding for the mutated ACVR1 protein, wherein the mutation is a R206H mutation, a Q207E mutation, a G328W mutation, a G328E mutation, a G356D mutation, or a combination thereof in other embodiments, or the nucleotides disclosed in Table 1. In one embodiment, the term "amplification" or "amplify" refers to one or more methods known in the art for copying a target nucleic acid, thereby increasing the number of copies of a selected nucleic acid sequence. Amplification may be exponential in one embodiment, or linear in another. In one embodiment, a target nucleic acid may be either DNA or RNA. The sequences amplified in this manner form an "amplicon." While the exemplary embodiments described herein relate to amplification using the polymerase chain reaction ("PCR"), numerous other methods are known in the art for amplification of nucleic acids (e.g., isothermal methods, rolling circle methods, etc.) and are considered within the scope of the present invention. The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 June 1; 29(11):E54-E54;

Hafner et al., Biotechniques 2001 April; 30(4):852-6, 858, 860 passim; Zhong et al., Biotechniques 2001 April; 30(4): 852-6, 858, 860.

In another embodiment, real time PCR is used in the methods of the invention. The term "real time PCR" refers in one embodiment to the process where a signal emitted from the PCR assay is monitored during the reaction as an indicator of amplicon production during each PCR amplification cycle (i.e., in "real time"), as opposed to conventional PCR methods, in which an assay signal is detected at the endpoint of the PCR reaction. Real time PCR is based in one embodiment on the detection and quantitation of a fluorescent reporter. The signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. For a general description of "real time PCR" see Dehe et al. J. Virol. Meth. 102:37-51 (2002); and Aldea et al. J. Clin. Microbiol. 40:1060-1062 (2002) (referring to the "LightCycler," where real-time, kinetic quantification allows measurements to be made during the log-linear phase of a PCR).

In one embodiment, real time PCR or other detection methods are used to detect the mutated ACVR1 protein, wherein the mutation is a R206H mutation, a Q207E mutation, a G328W mutation, a G328E mutation, a G356D mutation, or a combination thereof in other embodiments, or the nucleotides disclosed in Table 1, in the sample collected from the subject. In another embodiment, molecular beacons, specific for the mutated ACVR1 protein, wherein the mutation is a R206H mutation, a Q207E mutation, a G328W mutation, a G328E mutation, a G356D mutation, or a combination thereof in other embodiments, or the nucleotides disclosed in Table 1, are used as part of the methods and kits of the invention, wherein samples are split and the detectable signal from the bound molecular beacon, or labeled antibody, which could either be monoclonal or polyclonal antibody or a fragment thereof (F(ab') e.g.), is compared with a sample following digestion with an endonuclease. In one embodiment, the concentration of mutated ACVR1 is an indication of FOP in the subject, which could be sporadic FOP in one embodiment, or inherited FOP in another embodiment.

In one embodiment, any of the mutations described herein resulting in a mutated Activin A type I receptor (ACVR1), affects the Activin A type I receptor (ACVR1) to enhances activity or signaling of bone morphogenetic protein (BMP). In another embodiment, a combination of mutations on ACVR1 will creates a different degree of activity or signaling of BMP. Accordingly, in another embodiment, a mutated ASCVR1 is selected to yield optimal activation or in another embodiment, optimal signaling enhancing BMP. In one embodiment, a single mutation on ACVR1, or in another embodiment, all described mutations are encompassed in the mutated ACVR1 administered to a subject for enhancing BMP according to the methods provided herein. Accordingly and in another embodiment, provided herein is a In one embodiment, the cells used for the methods of the invention are obtained from a sample given by the subject. The sample to be analyzed may consist in one embodiment of, or comprise blood, sera, urine, mucosa, feces, epidermal sample, skin sample, cheek swab, sperm, amniotic fluid, cultured cells, bone marrow sample or chorionic villi, and the like. A biological sample may be processed in another embodiment to release or otherwise make available a nucleic acid or a protein for detection as described herein. Such processing may include in one embodiment steps of nucleic acid manipulation, e.g., preparing a cDNA by reverse transcription of RNA from the biological sample. Thus, the nucleic acid to be amplified in one embodiment by the methods of the invention may be DNA or RNA.

In one embodiment, the invention provides a method of treating Fibrodysplasia Ossificans Progressiva (FOP) in a subject, comprising the step of administering to said subject a siRNA against a nucleic acid encoding a mutated Activin A type I receptor (ACVR1) gene, and a wild-type Activin A type I receptor protein (ACVR1) as set forth in SEQ ID NO.26.

In one embodiment, the agent used in the compositions described herein, which are utilized in the methods provided herein, is a siRNA. In another embodiment, the agent capable of inhibiting the expression of mutated ACVR1 is a polyamide. In another embodiment, the agent capable of inhibiting the expression of mutated ACVR1 is a triple-helix-forming agent. In another embodiment, the agent capable of inhibiting the expression of mutated ACVR1 is an antisense RNA. In another embodiment, the agent capable of inhibiting the expression of mutated ACVR1 is a synthetic peptide nucleic acids (PNAs). In another embodiment, the agent capable of inhibiting the expression of mutated ACVR1 is an agRNA. In another embodiment, the agent capable of inhibiting the expression of mutated ACVR1 is a LNA/DNA copolymer. In another embodiment, the agent capable of inhibiting the expression of mutated ACVR1 is a small molecule chemical compounds, or a combination thereof.

In one embodiment, the term "siRNA" refers to RNA interference, which in one embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response.

In one embodiment, the term "conserved", refers to amino acid sequences comprising the peptides or nucleotides described herein, which remain in one embodiment, essentially unchanged throughout evolution, and exhibit homology among various species producing the protein.

The presence of long dsRNAs in cells stimulates in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression, which, in another embodiment is the gene encoding the mutated ACVR1 protein described herein.

In one embodiment, the siRNA of a mutated ACVR1 gene exhibit substantial complimentarity to its target sequence. In another embodiment, "complementarity" indicates that the oligonucleotide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of a mutated ACVR1 gene, is sufficiently complimentary to its target sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribo-nucleic acids, and the like. In one embodiment, the siRNAs used in the compositions and methods of the invention, are nucleic acid sequences.

In one embodiment, minor groove-binding N-methyl pyrrole (Py) and N-methylimidazole (Im) polyamides (peptides) uniquely recognize each of the four Watson-Crick base pairs. Antiparallel pairing of imidazole with pyrrole (Im/Py) recognizes in one embodiment, a G-C base pair, whereas in another embodiment, a Py/Py pair recognizes either an A-T or T-A base pair. The binding constant and sequence-specificity of the Py-Im hairpin polyamides are similar to that of a transcription factor. Therefore, many genes are silenced, in other embodiments, by competitive binding of Py-Im hairpin polyamides to their regulatory sequences. Gene expression is controlled in one embodiment, by a combination of multiple common trascription factors. In one embodiment, inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence. In one embodiment, the agent used to silence the mutated ACVR1 in the methods, kits and compositions described herein, is Py-Im polyamide specific for the gene's coding region, or to regulatory sequences that is unique to the mutated ACVR1 in another embodiment. In one embodiment, the agent used to silence the mutated ACVR1 in the methods, kits and compositions described herein, is a synthetic polyamide nucleic acid (PNA) specific for the coding region of the gene encoding the mutated ACVR1, or to its unique regulatory sequences in another embodiment.

In one embodiment, the polyamides used in the compositions and methods described herein, which, in another embodiment are referred to as "peptide nucleic acid" (PNA) or "synthetic peptide nucleic acids", are alkylating Py-Im polyamides that show sequence-specific DNA alkylation. In another embodiment, alkylation of a template strand in the gene encoding mutated ACVR1, by Py-Im polyamide-cyclopropylpyrroloindole (CPI) conjugates with a vinyl linker results in the production of truncated mRNA, effectively inhibiting transcription of the gene encoding mutated ACVR1 in vitro. In one embodiment, Py-Im tetra-hydro-cyclo-propabenzindolone (CBI) conjugates with indole linkers are the alkylating polyamides used as the agent capable of inhibiting the expression or function of the mutated ACVR1, because indole-CBI has increased chemical stability under acidic and basic conditions.

In another embodiment, oligodeoxynucleotides utilized in methods and compositions described herein inhibit cellular transcription by binding to duplex DNA to form a triple helix. Due to the possibility of long-term inhibition of the gene product, oligodeoxynucleotides that can bind duplex DNA have advantages over those that bind mRNA or proteins. These oligodeoxynucleotides are called in one embodiment, triplex forming oligonucleotides (TFOs). By using DNA-specific TFOs, the inhibition of expression of several cellular genes has been demonstrated, including the oncogene, c-myc, the human immunodeficiency virus-1, the alpha chain of the interleukin 2 receptor, the epidermal growth factor receptor, the progesterone responsive gene and the mouse insulin receptor. In one embodiment, the oligonucleotides used in the methods and compositions described herein, can bind to duplex DNA and form triple helices in a sequence-specific manner and will silence expression or function of the mutated ACVR1.

In one embodiment, homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one embodiment, an AT base pair is recognized by a T; and a GC base pair by a C that is protonated at N3$^+$. In another embodiment, homopurine strands specifically form a DNA triplex in which the AT base pair is contacted by an A; and the GC base pair by a G. In one embodiment, the agent administered in the methods described herein and which is capable of inhibiting the expression or function of the mutated ACVR1 is a triple-helix-forming agent. In another embodiment, the triple-helix-forming agents are olygonucletides. In one embodiment, oligonucleotide-mediated triplex formation prevent transcription factor binding to promoter sites and block mRNA synthesis in vitro and in vivo. In another embodiment, DNA intercalating or cross-linking agents are used to prolong oligonucleotide-duplex interactions.

In one embodiment, the term "TFO" or "triplex forming oligonucleotide" refers to the synthetic oligonucleotides of the present invention which are capable of forming a triple helix by binding in the major groove with a duplex DNA structure.

In one embodiment oligomeric antisense compounds, particularly oligonucleotides, are used in modulating the function of nucleic acid molecules encoding mutated ACVR1, ultimately modulating the amount of the pathogenic autoantibody produced. This is accomplished by providing antisense compounds which specifically hybridize with one or more nucleic acids encoding mutated ACVR1. In one embodiment, the terms "target nucleic acid" and "nucleic acid encoding mutated ACVR1" encompass DNA encoding mutated ACVR1, RNA (including pre-mRNA and mRNA) transcribed from such DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of mutated ACVR1. In one embodiment, inhibition of gene expression is preferred and mRNA is a preferred target. In one embodiment, since many genes (including VH3-8, VH3-07, or VH1-4M28 genes, or their combination) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. In one embodiment, the target is a nucleic acid molecule encoding mutated ACVR1. The targeting process also includes in another embodiment, determination of a site or sites within this gene for the antisense interaction to occur such that the desired effect, e.g., inhibition of expression of the protein such as mutated ACVR1, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes). In another embodiment, "start codon" and "translation initiation codon" refer to the codon or codons that are used in vivo to initiate translation of an mRNA molecule transcribed from a mutated ACVR1, regardless of the sequence(s) of such codons.

In certain embodiments, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer in one embodiment, to a portion of such a mRNA or gene that encompasses from about 25 to about 50 contiguous nucleotides in either direction (i.e., 5' or 3') from a translation initiation codon. In another embodiment, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," refers in one embodiment to the region between the translation initiation codon and the translation termination codon, is a region which may be targeted effectively. Other target regions include in other embodiments, the 5' untranslated region (5'UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises in one embodiment, an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region is a preferred target region in one embodiment.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as PV or PF. Aberrant fusion junctions due to rearrangements or deletions are also preferred targets. In one embodiment, introns can also be effective, and therefore preferred, target regions for antisense compounds targeted, for example, to DNA or pre-mRNA.

Antisense compounds are used in one embodiment, as research reagents and diagnostics. In another embodiment, antisense oligonucleotides, which are able to inhibit gene expression, such as the gene encoding the mutated ACVR1, with extreme specificity, are used by those of ordinary skill to elucidate the function of particular genes. Antisense compounds are used in another embodiment, to distinguish between functions of various members of a biological pathway. Antisense modulation is, in one embodiment of the agents described in the methods and compositions described herein, being harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man. In one embodiment, antisense oligonucleotides are safely and effectively administered to humans. In one embodiment oligonucleotides are useful therapeutic modalities that can be configured to be useful in treatment regimes of cells, tissues and animals, especially humans In one embodiment, the term "treatment" refers to any process, action, application, therapy, or the like, wherein a subject, including a human being, is subjected to medical aid with the object of improving the subject's condition, directly or indirectly. In another embodiment, the term "treating" refers to reducing incidence, or alleviating symptoms, eliminating recurrence, preventing recurrence, preventing incidence, improving symptoms, improving prognosis or combination thereof in other embodiments.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term.

In one embodiment, the methods of the invention are used in combination with other therapeutic agents, such as, but not limited to bisphosphonates, which inhibits osteoclastic-mediated bone resorption. In another embodiment, the other therapeutic agent is Etidronate, which in yet another embodiment may be delivered to a subject in need thereof operably linked to an antibody, a fragment thereof or their combination as described hereinabove.

In one embodiment, the invention provides a method of of treating a pathology associated with heterotopic ossification in a subject, comprising the step of administering to said subject an therapeutically effective amount of siRNA against a nucleic acid encoding a mutated Activin A type I receptor (ACVR1), wherein the Activin A type I receptor (ACVR1) enhances activity or signaling of bone morphogenetic protein (BMP). In another embodiment, the pathology associated with heterotopic ossification is ossification resulting from hip replacement surgery, or valvular heart disease, closed head trauma, spinal cord injuries, sports injuries, blast injuries, or a combination thereof in other embodiments.

In one embodiment, the term "heterotopic ossification" refers to the frequent sequela of central nervous system injury. It is encountered in certain embodiments, in cases of spinal cord injury, head injury, cerebrovascular accident and burns. In one embodiment, neurogenic heterotopic ossification is not associated with local trauma. The incidence of heterotopic ossification in patients with a head injury has been reported to be between 1% and 70%. Factors such as length of coma in one embodiment, or depth of coma, level of spasticity and duration of immobility in other embodiments, accounting for the discrepancy in incidence. In one embodiment, osseous trauma is associated with an increased incidence of heterotopic ossification distal to the trauma site, or due to the extent of the original cerebral injury in other embodiment. In one embodiment, the onset of heterotopic ossification may be as early as two weeks postinjury and patients remain susceptible to its onset through the first nine months after injury. In one embodiment, alkaline phosphatase level is raised in the presence of calcium deposition, with the development of heterotopic ossification preceding the elevation of serum alkaline phosphatase. In one embodiment, the hip appears to be the most common site of heterotopic ossification formation, occurring with almost equal frequency in the upper extremities and at both the elbow and the shoulder from craniocerebral injury. At the first sign of heterotopic ossification, and in one embodiment, administration of siRNA of mutated ACVR1, as well as non-mutated ACVR1 is initiated because in some 16% of cases of heterotopic ossification, joint ankylosis will develop. In other embodiments, the siRNA of mutated and non-mutated ACVR1 are administered either alone or with etidronate disodium therapy. In some patients treated with etidronate disodium, heterotopic ossification will continue to develop and it appears that a dosage of 20 mg per kg of body weight and a longer period of treatment may be necessary. In a combination therapy using the methods of the invention, it is possible that ossification will be inhibited, eliminated or retarded to the point where etidronate dosage can be cut back or eliminated in certain embodiments.

In one embodiment, the ossification pathology is the result of myositis ossificans traumatica, referring in another embodiment, to heterotopic bone formation that results from trauma to muscle tissue. The highest incidence of myositis ossificans traumatica occurs in the quadriceps muscle, while the next highest occurs in the brachialis muscle. At the first sign of heterotopic ossification, and in one embodiment, administration of siRNA of mutated ACVR1, as well as non-mutated ACVR1 is initiated because in some 16% of cases of heterotopic ossification, joint ankylosis will develop. In other embodiments, the siRNA of mutated and non-mutated ACVR1 are administered either alone or with etidronate disodium therapy.

Neurogenic Para Osteo-Arthropathies (NPOA) occurs in patients with brain or spinal cord injury, hemiplegias, various encephalopathies, tetanus or neurological disregulation. In this process, new bone referred to as "osteoma" in one embodiment, forms in extraskeletal areas which in normal condition do not ossify. In other embodiments, NPOA is referred to as: neurogenic osteoma, ossifying myositis in paraplegic, ectopic ossification, heterotopic ossification, etc. NPOAs have been described in other embodiments, capable of being treated with the methods described hereinabove, as complications of many systemic diseases, acute pancreatitis, toxic syndromes and others.

In one embodiment, the invention provides a method of enhancing activity or signaling of bone morphogenetic protein (BMP) in a cell, comprising contacting the cell with an effective amount of a mutated ACVR1 protein, wherein said protein enhances activity or signaling of bone morphogenetic protein (BMP). In another embodiment, the mutation results in a R206H mutation, a Q207E mutation, a G328W mutation, a G328E mutation, a G356D mutation, or a combination thereof on the Activin A type I receptor protein (ACVR1).

In another embodiment, the method of enhancing activity or signaling of bone morphogenetic protein (BMP) in a cell, comprising contacting the cell with an effective amount of a mutated ACVR1 protein, wherein said protein enhances activity or signaling of bone morphogenetic protein (BMP), wherein the mutation results in a R206H mutation, a Q207E mutation, a G328W mutation, a G328E mutation, a G356D mutation, or a combination thereof on the Activin A type I receptor protein (ACVR1), is used for the treatment of traumatic or congenital amputations, congenital malformations of the spine or limbs, spinal fusions, non-union fracture, osteoporosis, or a combination thereof.

In one embodiment, enhancing activity or signaling of morphogens provided herein stimulate the proliferation, growth and differentiation of osteoblasts in vitro and in another embodiment, can induce bone formation in osteoporotic bone tissue in vivo when provided systemically to a mammal, or directly to bone tissue, without an associated matrix carrier. In one embodiment, enhancing activity or signaling of the morphogens inhibit multinucleation of activated early mononuclear phagocytic cells.

The bone morphogenetic proteins (BMPs) are a group of activin proteins that in one embodiment, induce de novo cartilage and bone formation, and appear to be essential for skeletal development during mammalian embryogenesis (Wang, Trends Biotechnol. 11, 379, 1993). Due to their osteoinductive properties the BMPs are of clinical interest. In one embodiment, early in the process of fracture healing the concentration of bone morphogenetic protein-4 (BMP-4) increases dramatically. In another embodiment upregulation of BMP-4 transcription promotes bone healing in mammals. In another embodiment, enhancing activity or signaling of BMP may play an important role in bone remodeling and fracture repair, which in another embodiment, may be achieved by the methods described herein.

In one embodiment, the treatment methods described herein further comprise administering to the subject a signal transduction inhibitor or various signal transduction inhibitors designed or selected specifically to block the activity of the various mutated ACVR1 proteins or, in another embodiment, leave the unmutated wild ACVR1 molecules unimpaired to carry-out their normal function. In one embodiment the signa transduction inhibitor is administered in combination with the monoclonal antibodies and siRNA specific against the mutated ACVR1 described herein.

In one embodiment, Inhibins are endogenous antagonists of activin signaling. In one embodiment, Inhibin B and inhibin A are heterodimeric proteins in the TGFβ superfamily composed of αβB or αβA subunits, respectively. Inhibins are recognized as regulators of reproduction that antagonistically modulate in one embodiment, the endocrine interaction of the pituitary and gonadal systems, which are produced by the gonads in response to FSH and act at the pituitary to attenuate activin effects such as BMP's in one embodiment. Activins, like BMPs, stimulate target cells by assembling receptor complexes containing type I receptors such as ACVR1 in one embodiment, at the cell membrane. In these ligand-receptor complexes, distinct activin-specific type I receptors are activated and in turn activate activin-specific Smads. In one embodiment, inhibins are used in the combination therapy according to the treatment embodiments described herein, as a signal transduction antagonist.

In one embodiment, Follistatin is a natural antagonist that binds activin with high affinity and neutralizes its biological activities by preventing activin interaction with its membrane receptors. In another embodiment, Follistatin is a single-chain glycoprotein of 35 kDa which is composed of four cysteine-rich domains, three of which are homologous and highly conserved. In one embodiment follistatin and other follistatin-related molecules act by regulating the availability of TGF-β.-related or other growth factors in another embodiment, thereby influencing cellular migration, proliferation, and differentiation.

In another embodiment, antagonists of BMP signal transduction activity include fetuin glycoprotein, also known as .alpha.2-HS glycoprotein in humans, and the DAN family of BMP antagonists, such as noggin, chordin, follistatin, and gremlin. In one embodiment, noggin, or chordin, follistatin, gremlin or their combination are administered in the methods of treating FOP, or other heterotopic ossification pathgologies described herein. In one embodiment, Gremlin regulates outgrowth, chondrogenesis and programmed cell death in the developing limb or regulation of the onset of neural crest migration by coordinated activity of BMP4 and noggin in the dorsal neural tube. In another embodiment, fetuin blocks osteogenesis, or ossification and is used in inhibiting signal transduction as described herein. In one embodiment, Noggin binds several BMPs with very high (picomolar) affinities, with a marked preference for BMP2 and BMP4. By binding tightly to BMPs, Noggin prevents BMPs from binding their receptors in one embodiment, acting as a signal transduction inhibitor. In another embodiment, Chordin also antagonizes BMP signaling by directly binding BMP proteins, thereby preventing receptor activation, such as ACVR1 receptor, or in another embodiment, a mutated ACVR1. Noggin interactions has been restricted in one embodiment, to a subset of BMPs mainly BMP4 in one embodiment.

In one embodiment, the kits described herein, use the compositions described herein and may be used to carry out the methods described herein.

In one embodiment, the invention provides a kit for diagnosing Fibrodysplasia Ossificans Progressiva (FOP) in a subject, comprising: an antibody, a fragment thereof, or a molecular beacon, said antibody, fragment thereof, or molecular beacon specifically reactive with a mutated Activin A type I receptor protein (ACVR1), or a gene encoding said mutated Activin A type I receptor protein (ACVR1).

In one embodiment, the antibody, fragment thereof, or molecular beacon which is specifically reactive with a mutated Activin A type I receptor protein (ACVR1), or a gene encoding said mutated Activin A type I receptor protein (ACVR1), is encompassed in the embodiments of the compositions described herein.

In one embodiment, the kits of the invention may further comprises a positive or negative standards, wherein the standard can be assayed and compared to the test sample. It is to be understood that the kits of the invention may be modified and marketed for particular use, which in one embodiment are FOP-specific, or sporadic FOP specific or inherited FOP specific in other embodiments. In one embodiment, the kit is specific for pathology associated with heterotopic ossification such as ossification resulting from hip replacement surgery, valvular heart disease, closed head trauma, spinal cord injuries, sports injuries, blast injuries, or a combination thereof in other embodiments.

In one embodiment, the results obtained are compared to a standard, which, in another embodiment, may comprise a series of standards, which, in another embodiment is used in the kits of the invention for quantification of differential expression. In one embodiment, the standard may comprise any embodiment listed herein, or in another embodiment, will be suitable for a particular application of the kit.

In one embodiment, the kit of the invention may further comprise a software package contained on a computer storage medium, with a program for correlating values obtained with a standard, for storing and comparing, by date, or in another embodiment for extrapolating results obtained.

In the methods and kits according to embodiments of the present invention, data relating to values obtained for the parameters for malignant and non-malignant samples analyzed may be provided in a database such as Microsoft Access, Oracle, other SQL databases or simply in a data file. The database or data file may contain in one embodiment, a patient identifier such as a name or number, the values obtained, patient prognosis, age of onset of symptoms, therapy regimen, and other identifying and relevant characteristics, as will be understood by one skilled in the art. The database may contain, in other embodiments, the change in any of the parameters analyzed, as a function of time, or therapy regimen, or a combination thereof. In one embodiment, the methods and kits of this invention may further comprise accessing a memory, or a means thereto for storing the obtained values for the parameters, and other data as described herein. In another embodiment, the methods of this invention may further comprise generating and graphically displaying the values obtained. In one embodiment, the analysis is executed by a processor or a virtual computer program In one embodiment the software incorporates statistical tools for determining the significance of the findings. Statistical significance is determined, in other embodiments, by conducting pairwise comparisons, and determining a p value. See, e.g., Dowdy and Wearden, Statistics for Research, John Wiley & Sons, New York, 1983. In one embodiment, a p value of 0.1, 0.05, 0.025, 0.02, 0.01, 0.005, 0.001, 0.0001, or less is indicative of a significant difference.

In one embodiment, the invention provides a transgenic mouse which expresses a transgene integrated into its genome, wherein the transgene comprises DNA encoding a mutant ACVR1 protein, wherein said mutated ACVR1 results in enhanced activity or signaling of bone morphogenic protein (BMP).

In another embodiment, the invention provides a transgenic mouse whose genome comprises a homozygous disruption of an Activin A type I receptor (ACVR1) gene whereby said Activin A type I receptor (ACVR1) gene does not produce functional Activin A type I receptor protein (ACVR1), wherein the mouse's genome additionally comprises a DNA sequence encoding a mutated Activin A type I receptor protein (ACVR1), said mouse showing one or more defects similar to the pathological features of a patient afflicted with heterotopic ossification.

In one embodiment, the wild-type ACVR1 gene is knocked out. In one embodiment, the term "knock-out" refers to an alteration in the nucleic acid sequence that educes the biological activity of the polypeptide normally encoded therefrom by at least 80% compared to the unaltered gene. The alteration may be an insertion in one embodiment, or deletion, frameshift mutation, or missense mutation and their combination in other embodiments. In one embodiment, the alteration is an insertion or deletion, or is a frameshift mutation that creates a stop codon. In another embodiment, "reduced biological activity" refers to the functional activity of a given protein in a standardized quantity of tissue or cells. The activity of a protein, as a whole, in such a sample can be modified as a result of a change in the quantity of the given protein present (e.g., as a result of change in gene expression) or as a result of a change in the function of each protein molecule present in the sample (e.g., as a result of an alteration in amino acid sequence).

In one embodiment, the term "transgenic" refers to any animal which includes a nucleic acid sequence which is artificially inserted into a cell and becomes a part of the genome of the animal that develops from that cell. Such a transgene may be partly or entirely heterologous to the transgenic animal. Although transgenic mice represent one embodiment, other transgenic mammals including, without limitation, transgenic rodents (for example, hamsters, guinea pigs, rabbits, and rats), and transgenic pigs, cattle, sheep, and goats are included in the definition.

As used herein, "subject" refers to a human or any other animal which contains a mutated ACVR1 that can be detected using the molecular beacons, methods and kits described herein. A subject can be a patient, which refers to a human presenting to a medical provider for diagnosis or treatment of a disease. A human includes pre and post natal forms. In one embodiment, subjects are humans being tested for the efficacy of chemotherapy for the treatment of cancer.

The term "about" as used herein means in quantitative terms plus or minus 5%, or in another embodiment plus or minus 10%, or in another embodiment plus or minus 15%, or in another embodiment plus or minus 20%.

The following examples are presented in order to more fully illustrate the preferred embodiments of the invention. They should in no way be construed, however, as limiting the broad scope of the invention.

EXAMPLES

Example 1: a Mutation in the BMP Type I Receptor ACVR1 Causes Inherited and Sporadic Fibrodysplasia Ossificans Progressiva Materials and Methods Subjects and Clinical Evaluation Blood samples were obtained following informed consent from individuals and/or their parents in accordance with a protocol approved by the Institutional Review Board of the University of Pennsylvania School of Medicine.

Linkage Studies

Genomic DNA was isolated directly from blood samples, buccal swabs, or from lymphoblast cell lines (LCLs) using QIAamp DNA Blood reagents (Qiagen) and standard protocols. EBV-transformed LCLs were established by standard protocols. Some samples were whole genome-amplified using Repli-G reagents (Molecular Staging Inc.) and standard protocols. Genome wide linkage analysis was carried out through the University of Utah School of Medicine Genomics Core Facility using an ABI 3130xl Genetic Analyzer and scoring with ABI GeneMapper v.3. All families were genotyped using 400 microsatellite markers from the ABI Prism linkage mapping set v.2.5 (medium density 10 cM set). For fine mapping, markers selected from the Marshfield genetic map were used. Family A genotyping data from an earlier study[1] was integrated into this analysis. Genehunter v.2 software was used to calculate multipoint parametric LOD scores. A model of an autosomal dominant trait with 100% penetrance of the FOP gene was assumed, with a population prevalence of FOP of 1 per million. SNP genotyping was conducted through the University of Pennsylvania School of Medicine Microarray Core Facility using the Affymetrix GeneChip Mapping 10K Array and Genespring GT software (Agilent Technologies)

Mutation Analysis

Mutations in ACVR1 were screened for by PCR-amplification of genomic DNA from blood or LCLs corresponding to the 9 exons containing protein coding sequences (ACVR1 Transcript Report, Ensembl v35), using exon-flanking primers (see Table 1 for primer sequences). DNA sequence analysis of genomic DNA was carried out on an ABI3730 sequencer through the University of Pennsylvania School of Medicine DNA Sequencing Facility. Sequence data were analyzed using 4Peaks software v.1.6 (http://www.mekentosj.com/4peaks/).

Differences in restriction endonuclease recognition sites were identified using MacVector v.7.2 software (ABI). We amplified 0.1 ug of genomic DNA using primers for protein coding exon 4. Following agarose gel electrophoresis, the PCR products (350 bp) were recovered from agarose using QIAquick Gel Extraction reagents (Qiagen). Purified PCR product was digested with either HphI (5 U/ul) or Cac8I (4 U/ul) (both from New England Biolabs) at 37° C. for 2 hours. Fragments were resolved on 3% NuSieve 3:1 agarose (FMC BioProducts) gels with 100 bp ladder (New England Biolabs) as size markers.

Cell Culture and RNA Analysis

LCLs from 4 FOP patients and 4 controls were grown in RPMI 1640 media with 15% FBS. Total RNA was extracted from $10^7$ cells using RNeasy reagents (Qiagen) and performed reverse transcription using SuperScript III (Invitrogen). PCR was used amplify the region corresponding to protein coding exon 4 with specific primers (see Table 1 for primer sequences) and Taq DNA polymerase (Invitrogen) then directly sequenced the amplified cDNA as described above.

Molecular Modeling of Protein Structure

Structural protein homology modeling was based on the PDB structure for type I TGFβ receptor kinase which is 66% identical to ACVR1 residues 178-498. This region includes the serine/threonine protein kinase catalytic domain and the GS motif with arginine residues at ACVR1 positions 202 and 206. ACVR1 amino acid 178-498 sequence was submitted to PredictProtein (http://www.embl-heidelberg.de/predictprotein/submit_def.html), CPHmodels homology-modeling server (http://www.cbs.dtu.dk/services/

TABLE 1

ACVR1 primers for genomic DNA PCR amplification.

| Protein coding exon # | Forward primer | Reverse primer | PCR product size |
|---|---|---|---|
| Exon 1 | 5'-GGCAGTTTGAAGGTGGTATG-3' (SEQ ID NO. 1) | 5'-ACCCAAAAAGATGTGAGTCAC-3' (SEQ ID NO. 11) | 184 bp |
| Exon 2 | 5'-ATATGAACACCACAGGGGG-3' (SEQ ID NO. 2) | 5'-CCTTTCTGGTAGACGTGGAAG-3' (SEQ ID NO. 12) | 449 bp |
|  | 5'-TTTTTTCCCCTTCCTTTCTCTC-3' (SEQ ID NO. 3) | 5'-CAGGGTGACCTTCCTTGTAG-3' (SEQ ID NO. 13) | 438 bp |
| Exon 3 | 5'-AATTCCCCCTTTTCCCTCCAAC-3' (SEQ ID NO. 4) | 5'-TAAGAACGTGTCTCCAGACACC-3' (SEQ ID NO. 14) | 300 bp |
| Exon 4 | 5'-CCAGTCCTTCTTCCTTCTTCC-3' (SEQ ID NO. 5) | 5'-AGCAGATTTTCCAAGTTCCATC-3' (SEQ ID NO. 15) | 350 bp |
| Exon 5 | 5'-TCCCAAGCTGAGTTTCTCC-3' (SEQ ID NO. 6) | 5'-AGAGCAAAGGCAGACAATTG-3' (SEQ ID NO. 16) | 346 bp |
| Exon 6 | 5'-GACATTTACTGTGTAGGTCGC-3' (SEQ ID NO. 7) | 5'-AGAGATGCAACTCACCTAACC-3' (SEQ ID NO. 17) | 438 bp |
| Exon 7 | 5'-TGGGGTTGGTTTAAAATCCTTC-3' (SEQ ID NO. 8) | 5'-AGGTAGCTGGATCAAGAGAAC-3' (SEQ ID NO. 18) | 337 bp |
| Exon 8 | 5'-CACATTATAACCTGTGACACCC-3' (SEQ ID NO. 9) | 5'-ATACCAGTTGAAACTCAAAGGG-3' (SEQ ID NO. 19) | 299 bp |
| Exon 9 | 5'-GTATTGCTGCTTTTGGCAC-3' (SEQ ID NO. 10) | 5'-CAGTCCCTACCTTTGCAAC-3' (SEQ ID NO. 20) | 700 bp |

Protein coding exon 1 contains the ATG protein start codon. The R206H mutation is in protein coding exon 4.

CPHmodels/) and the SWISS-MODEL homology-modeling server (http://swissmodel.expasy.org/) Visualization used the DeepView Swiss PDB Viewer.

Gene and Protein Analysis

Genes in the linked region were identified through the National Center for Biotechnology Information Entrez Map Viewer and the UCSC Genome Browser. The intron-exon boundaries of the ACVR1 gene were obtained through GenBank, Ensembl Human Genome Server, and the University of Santa Cruz. Genomic DNA positions of markers and the ACVR1 gene are from the UCSC Genome Browser (May 2004, Build 35). Transcript and exon information is from Ensembl (Gene ID ENSG00000115170; transcript ID ENST00000263640) which reports 11 exons for ACVR1 (exons 1 and 2 contain only 5'UTR; the protein start site is in exon 3), consistent with GenBank BC033867, full length cDNA clone). All databases are consistent for the sequence information for the 9 exons containing protein-coding sequences, however, additional/alternate exons containing 5'UTRs are reported. ACVR1 protein ID is Q04771 (Pfam, SWISSPROT). Clustal W (with the MacVector v 7.2 software program) was used for multiple protein alignment using sequences from GenBank.

GenBank Accession Numbers

ACVR1 cDNA, NM_001105; ACVR1 coding region, NT_005403. ACVR1 protein for *Homo sapiens* (human), NP_001096; *Mus musculus* (mouse), NP_031420; *Rattus norvegicus* (rat), NP_077812; *Canis familiaris* (dog), XP_856152; *Bos taurus* (cow), NP_788836; *Gallus gallus* (chick), NP_989891; *Xenopus laevis* (frog), AAH88947; *Danio rerio* (zebrafish), NP_571420. *Fugu rubripes* (pufferfish) sequence was from Ensembl prediction SINFRUG00000134562.

Results

The formation of bone where it is neither needed nor wanted can lead to devastating consequences. FOP (OMIM 135100) is the most severe and disabling disorder of extraskeletal (heterotopic) ossification in humans.[1] Heterotopic ossification in FOP begins in childhood and can be induced by trauma, or may occur without warning. Bone formation is episodic and progressive, leading to extra-articular ankylosis of all major joints of the axial and appendicular skeleton, rendering movement impossible (FIG. 1a)

The severe disability of FOP results in low reproductive fitness and few examples of inheritance are known. When observed, genetic transmission is autosomal dominant and can be inherited from either mothers or fathers. With the identification of additional pedigrees, a more conservative genome-wide linkage analysis was conducted using a subset of five families with the most stringent and unambiguous features of FOP (congenital malformation of the great toes and progressive heterotopic ossification in characteristic anatomic patterns; FIG. 1a, b) in all affected family members.

Characteristic Clinical Features of FOP

FOP is the most severe and disabling disorder of extraskeletal (heterotopic) ossification in humans.[1] Heterotopic ossification in FOP begins in childhood and can be induced by trauma, or may occur without warning. Bone formation is episodic, progressive, and extensive, leading to the extra-articular ankylosis of all the major joints of the axial and appendicular skeleton, rendering movement impossible (FIG. 1a). Flareups of FOP arise and progress in a well-defined spatial pattern that result in ribbons, sheets, and plates of bone that fuse the joints of the axial and appendicular skeleton, entombing the patient in a "second skeleton" of heterotopic bone. One of the more readily recognized skeletal malformations in FOP patients are great toe malformations of metatarsals and proximal phalanges that can occur along with microdactyly, fused interphalangeal joints, and hallux valgus deviations at the metatarsophalangeal joints (FIG. 1b). The severe disability of FOP results in low reproductive fitness and few examples of inheritance of FOP are known. Death often results by the fifth decade from thoracic insufficiency syndrome.[2] There is no effective prevention or treatment.

Descriptions of FOP Families.

The initial linkage analysis used four families that showed autosomal dominant inheritance of FOP-type heterotopic ossification, although not all affected individuals in each pedigree had characteristic malformation of the great toes. With the experience of examining more patients over time, concern was raised as to whether patients without both of these features could confound linkage analysis due to locus heterogeneity or mosaicism. This clinical information prompted the decision to use only a subset of families in whom all affected individuals had unambiguous features of malformed toes and progressive heterotopic ossification (FIG. 1a, b) in the present linkage analysis (FIG. 2a). A combined multipoint lod plot for the markers in the chromosome 2 FOP linkage region is shown in FIG. 2b.

Investigation of the ACVR1 c.617G>A (R206H) mutation in the five families used in the current linkage analysis show that all affected members have the mutation and none of the unaffected members available for examination carry the mutation. Of the four families used in the initial linkage study, Family 1 had unambiguous features of FOP in all affected individuals and was used in the current study (Family A in FIG. 2a). (Family numbers are those used in Feldman, G. et al. Fibrodysplasia ossificans progressiva, a heritable disorder of severe heterotopic ossification, maps to human chromosome 4q27-31. *Am. J. Hum. Genet.* 66, 128-135 (2000), which is hereby incorporated herein in its entirety; letters are used to identify families in the current study.) Family 2 showed ambiguous FOP features, with one member possessing only toe malformations without heterotopic ossification, while another had no toe malformation and mild heterotopic ossification that has not progressed. This family was not used in the current linkage analysis since every member did not fulfill the most stringent diagnostic criteria for FOP. No ACVR1 c.617G>A mutation was detected in any member of this family. In Family 3, FOP was inherited from mother to children and all had classic features of FOP (M. LeMerrer, personal communication). However, this family was not available for confirmational re-examination and was thus excluded from the current linkage analysis. Subsequent evaluation of Family 3 with chromosome 2 markers confirmed linkage to the FOP locus and all affected members of this family contain the ACVR1 c.617G>A mutation. Family 4 had two affected members, one with classic features of FOP (daughter), while the other (father) showed only mild evidence of heterotopic ossification with no toe malformation. The daughter was heterozygous for ACVR1 c.617G>A, while the father does not carry a germline mutation.

An additional very recently identified family consists of a father with FOP (deceased, unavailable for analysis), an unaffected mother, and two affected children with classic FOP features. This family shows linkage to the chromosome 2 FOP locus and both children are heterozygous for ACVR1 c.617G>A on the paternally inherited allele.

c.617G>a (R206H) Mutations in the ACVR1 Gene in Patients with FOP

The chromosome 2q FOP critical genomic region (FIG. 3a) spans ~23.9 Mb between markers rs1020088 (centromeric) at 150,654,341 bp and D2S1238 (telomeric) at 174, 505,230 bp as annotated by UCSC GenomeBrowser. The ACVR1 gene spans ~138.6 kb of genomic DNA (chromosome 2: 158,418,469-158,557,131). ACVR1 encodes a 509 amino acid protein that contains a ligand binding region, a transmembrane (TM) domain, a glycine-serine (GS) rich domain, and a protein kinase domain. The numbers above the protein representation in FIG. 3a indicate the amino acids included in each identified domain.

ACVR1 Gene Structure

The intron-exon boundaries of the ACVR1 gene were obtained through GenBank, Ensembl Human Genome Server, and the University of Santa Cruz. Transcript and exon information was obtained from Ensembl (Gene ID ENSG00000115170; transcript ID ENST00000263640) which reports 11 exons for ACVR1 (exons 1 and 2 contain only 5'UTR; the protein start site is in exon 3), consistent with GenBank BCO33867, full length cDNA clone. All databases for ACVR1 are consistent for the sequence information for the nine exons containing protein-coding sequences, however, additional/alternate exons containing 5'UTRs are reported through the University of Santa Cruz Genome Browser (12 exons with the protein start in exon 4) and GenBank (10 exons with the protein start in exon 2). The R206H mutation occurs in nucleotide 617 of ACVR1 cDNA (c.617G>A). [Notation follows standard nomenclature guidelines.]

Protein Structure Predictions

Structural protein homology modeling was used to determine possible biochemical consequences of the ACVR1 R206H mutation. While SWISS-MODEL analysis showed no deviation between proteins containing Arg206 or His206, both PredictProtein and CPHmodels predict a partial destabilization of the α-helix formed by ACVR1 amino acids 198-206 (FIG. 4). These models reveal that Arg202 and Arg206 are spatially orientated on the same helical face (i, i+4). Previous studies have demonstrated that the electrostatic effects of charged ion pairs can have significant helix stabilizing interactions between side chains when the spacing between residues is close to the helical repeat of 3.6 residues per turn (i.e. i, i+4). Additionally, polar side chains are often long, thus allowing their hydrophobic alkyl groups to interact favorably with nonpolar residues while keeping the polar parts free to interact with other polar groups. Side chains such as lysine and arginine can thus interact favorably with both polar and non-polar residues. Therefore, the shorter side chain of the R206H mutant is expected to cause a partial destabilization of the α-helix altering the electrostatic potential of the ACVR1 protein (FIG. 4).

Additionally the R206H mutation may impair protein-protein interactions with the GS domain. This 30 residue motif of the type I TGFβ receptor (TβR-I) kinase has two regulatory functions: (1) tight control over the basal state with FKBP12 binding to the unphosphorylated GS domain and creating a inhibitory wedge that prevents interactions with other proteins and, (2) a catalytically "open" form that binds ATP leading to protein-protein interactions with the Smad2 MH2 domains. Arginine-arginine pairs within a protein can stabilize complex formation between proteins or can stabilize regions of backbone structure through intramolecular interactions.

Figure 5:
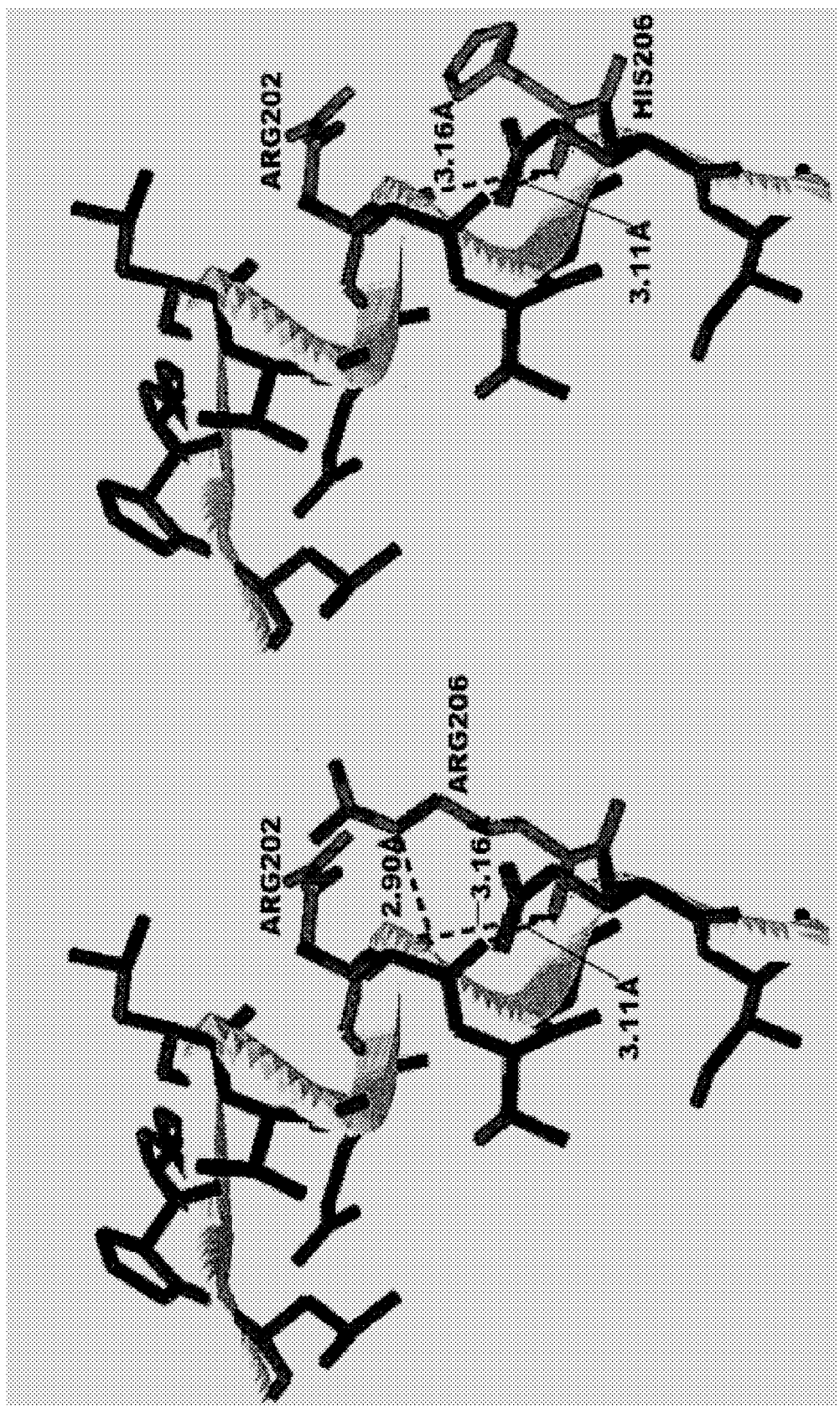
FIG. 5 shows the effect of the Arg206His mutation on the predicted protein structure of the ACVR1 ct-helix, residues 198-206. (a) Homology model of wild-type ACVR1 shows that the most likely conformation (lowest scoring rotamer) of the arginine 206 side chain predicts that it interacts with the a-helix backbone to stabilize the protein. (b) Homology model of mutant Arg206His ACVR1 shows that the most likely conformation (lowest scoring rotamer) of the histidine 206 side chain does not interact with the a-helix backbone which is predicted to result in partial destabilization of the protein.

The effect of the R206H mutation on the predicted protein structure of the ACVR1 α-helix, residues 198-206 is shown in FIG. 5. The homology model of wild-type ACVR1 shows that the most likely conformation (lowest scoring rotamer) of the arginine 206 side chain predicts that it interacts with the α-helix backbone to stabilize the protein. Homology model of mutant R206H ACVR1 shows that the most likely conformation (lowest scoring rotamer) of the histidine 206 side chain does not interact with the α-helix backbone which is predicted to result in partial destabilization of the protein.

The Arg>His amino acid change in codon 206 appears conservative in that one positively charged amino acid is substituted for another. (In fact, in human BMPRIA and BMPRIB, codon 206 is a lysine; see FIG. 6.) However, protein modeling predicts that the shorter histidine side chain will nevertheless alter protein structure and/or protein-protein interactions. Furthermore, a non-conservative (non-positively charged) amino acid change in codon 206 in one embodiment, may result in a lethal mutation.

Constitutively Activating Mutations in the GS Domain of Type I TGFβ Receptors

Type I TGFβ/BMP receptors contain a highly conserved 30 amino acid GS domain that is phosphorylated by ligand-bound type II receptors Amino acid substitutions in the GS domain (T204D) have been shown to lead constitutively activating forms of TβR-I (TGF-β type I receptor). (Codon 204 in TβR-I is analogous to codon 207 in ACVR1.).

Recurrent Mutations in Human Disease

The FOP R206H ACVR1 mutation is one of the most specific codons in the human genome to be associated with a disease phenotype.

Linkage Analysis (Continued)

This approach excluded the 4q27-31 region and identified linkage of FOP to 2q23-24 in the region flanked by markers D2S1399 and D2S1238 (FIG. 2a). SNP genotyping fine-mapped the linkage region between rs1020088 (150,654,341 bp) and D2S1238 (174,505,230 bp). The multipoint lod score was 2.3 at θ=0 (see FIG. 5).

Activin a Type I Receptor Gene (ACVR1; OMIM 102576; Also Known as Alk2 or ActRIA), a Receptor for Bone Morphogenetic Protein (BMP) is Associated with FOP No other genomic region showed consistent linkage in all five families. This genetic interval (FIG. 3a) includes the Activin A type I receptor gene (ACVR1; OMIM 102576; also known as Alk2 or ActRIA), a receptor for bone morphogenetic protein (BMP). ACVR1 is expressed in many tissues including skeletal muscle and chondrocytes. Constitutive activation of ACVR1 induces alkaline phosphatase activity in C2C12 cells, upregulates BMP4, downregulates BMP4 antagonists, expands cartilage elements, induces ectopic chondrogenesis, and stimulates joint fusions.[5,6] ACVR1 is therefore a strong candidate gene for FOP which is associated with similar clinical findings and dysregulation of the BMP signaling pathway.

DNA sequence analysis of all ACVR1 protein-coding exons and splice junctions (see Table 1) revealed the presence of the identical heterozygous single nucleotide change at cDNA position 617 (c.617G>A) in all examined familial and sporadic FOP patients (FIG. 2b). We found this mutation in all affected members of seven families, including all five families used for linkage analysis (FIG. 2a). Investigation of sporadic cases of FOP patients with unambiguous clinical features revealed the presence of the identical de novo mutation in 32 of 32 cases. The examined subjects with an ACVR1 c.617G>A mutation included a patient with a previously reported, but unverifiable, mutation in the Noggin gene. In addition to direct DNA sequence analysis, the G>A nucleotide change can be verified by differential restriction endonuclease digestion (FIG. 3a).

The c.617G>A nucleotide mutation was not found in any of 159 unaffected individuals (112 unrelated controls and 47 clinically unaffected family members of patients). Unaffected family members examined included the parents of six patients with sporadic FOP. Absence of the mutation in these parents as well as in unaffected members of the linkage pedigrees (FIG. 1c) support that this mutation is fully penetrant. The ACVR1 c.617G>A nucleotide variant is not reported in SNP databases.

Sporadic cases of FOP have been reported in all racial and ethnic groups and de novo ACVR1 c.617G>A mutations were found in all groups. The pedigrees examined by linkage include several ethnicities (African-American, American-European descent, European (United Kingdom), Korean, and Native Brazilian), and haplotype analysis of markers in the linked region (FIG. 2a) demonstrates no evidence of a founder effect for the mutation.

All publications, patents, and patent applications cited herein are hereby incorporated by reference in their entirety for all purposes.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A nucleic acid comprising a a double stranded DNA duplex comprising two complementary strands of DNA, wherein one of the two complementary strands of DNA contiguously encodes SEQ ID NO: 21 or a fragment thereof comprising SEQ ID NO: 42.

2. The nucleic acid of claim 1, wherein the nucleic acid is labeled with a detectable marker.

3. The nucleic acid of claim 2, wherein the detectable marker is a radioactive, colorimetric, luminescent, fluorescent marker, a photoluminescent dye, or a gold label.

4. A composition comprising a molecular beacon, said molecular beacon comprising: an oligonucleotide comprising a stem and a loop, and a detectable label, wherein the loop comprises at least 12 contiguous bases of SEQ ID NO: 34 or its complement, and wherein position 11 of SEQ ID NO: 34 is an A.

5. The composition of claim 4, wherein the oligonucleotide of said molecular beacon comprises a photoluminescent dye at its 5' or 3' end and a quenching agent at the opposite 3' or 5' end respectively, wherein said loop is 12-25 bases in length.

6. The composition of claim 5, wherein said photoluminescent dye is fluorescein, phycoerythrin, CY3, CY5, allophycocyanine, Texas Red, peridenin chlorophyll, cyanine, FAM, JOE, TAMRA, TET, VIC, or a combination thereof.

7. The composition of claim 5, wherein said quenching agent is EDANS, BHQ1, DABCYL, BODIPY FL, BH1, BH2, QSY7, or a combination thereof.

8. A method of diagnosing Fibrodysplasia Ossificans Progressiva (FOP) in a subject, comprising: contacting a biological sample from said subject with a molecular beacon of claim 4; and assaying for the presence of a mutated Activin A type I receptor protein (ACVR1) that encodes histidine at the position corresponding to position 206 of SEQ ID NO: 21, wherein the presence of the mutated Activin A type I receptor protein (ACVR1) in said sample indicates that said subject has Fibrodysplasia Ossificans Progressiva (FOP).

9. The method of claim 8, whereby the Fibrodysplasia Ossificans Progressiva (FOP) is inherited Fibrodysplasia Ossificans Progressiva (FOP).

10. The method of claim 8, whereby the Fibrodysplasia Ossificans Progressiva (FOP) is sporadic Fibrodysplasia Ossificans Progressiva (FOP).

11. The method of claim 8, whereby said molecular beacon further comprises a detectable label operably linked thereto.

12. The method of claim 11, whereby said label is an enzyme.

13. The method of claim 8, whereby said molecular beacon comprises: an oligonucleotide comprising a stem and a loop structure and having a photoluminescent dye at one of the 5' or 3' ends and a quenching agent at the opposite 3' or 5' ends.

14. The method of claim 8, further comprising amplifying a target sequence of said molecular beacon.

15. The method of claim 11, whereby said label is a radiolabel, a fluorophore, a peptide, an enzyme, a quantum dot, or a combination thereof.

16. The method of claim 15, whereby said quantum dot is CdSe.

17. The method of claim 13, whereby said photoluminescent dye is fluorescein, phycoerythrin, CY3, CY5, allophycocyanine, Texas Red, peridenin chlorophyll, cyanine, FAM, JOE, TAMRA, TET, VIC, or a combination thereof.

18. The method of claim 13, whereby said quenching agent is EDANS, BHQ1, DABCYL, BODIPY FL, BH1, BH2, QSY7, or a combination thereof.

19. A kit for diagnosing Fibrodysplasia Ossificans Progressiva (FOP) in a subject, comprising the composition of claim 4.

20. The kit of claim 19, wherein the detectable label is a radiolabel, a fluorophore, a peptide, an enzyme, a quantum dot, or a combination thereof.

21. The kit of claim 19, further comprising at least one standard, obtained from a subject, or pool of subjects, without Fibrodysplasia Ossificans Progressiva (FOP).

22. The kit of claim 19, further comprising at least one standard, obtained from a subject, or pool of subjects, with Fibrodysplasia Ossificans Progressiva (FOP).

23. The nucleic acid of claim 1, wherein one of the two complementary strands of DNA contiguously encodes SEQ ID NO: 21.

* * * * *

UNITED STATES PATENT AND TRADEMARK OFFICE
CERTIFICATE OF CORRECTION

PATENT NO. : 10,106,852 B2
APPLICATION NO. : 14/521143
DATED : October 23, 2018
INVENTOR(S) : Frederick S. Kaplan et al.

Page 1 of 1

It is certified that error appears in the above-identified patent and that said Letters Patent is hereby corrected as shown below:

In Column 1, Line 15, please insert the following:
--GOVERNMENT INTEREST STATEMENT
This invention was made with government support under AR041916 awarded by the National Institutes of Health. The government has certain rights in the invention.--

Signed and Sealed this
Eighth Day of October, 2019

Andrei Iancu
*Director of the United States Patent and Trademark Office*

SEQUENCE LISTING

```
<160> NUMBER OF SEQ ID NOS: 49

<210> SEQ ID NO 1
<211> LENGTH: 20
<212> TYPE: DNA
<213> ORGANISM: Homo sapiens

<400> SEQUENCE: 1
ggcagtttga aggtggtatg                                               20

<210> SEQ ID NO 2
<211> LENGTH: 19
<212> TYPE: DNA
<213> ORGANISM: Homo sapiens

<400> SEQUENCE: 2
atatgaacac cacaggggg                                                19

<210> SEQ ID NO 3
<211> LENGTH: 22
<212> TYPE: DNA
<213> ORGANISM: Homo sapiens

<400> SEQUENCE: 3
tttttccccc ttcctttctc tc                                            22

<210> SEQ ID NO 4
<211> LENGTH: 22
<212> TYPE: DNA
<213> ORGANISM: Homo sapiens

<400> SEQUENCE: 4
aattccccct tttccctcca ac                                            22

<210> SEQ ID NO 5
<211> LENGTH: 21
<212> TYPE: DNA
<213> ORGANISM: Homo sapiens

<400> SEQUENCE: 5
ccagtccttc ttccttcttc c                                             21

<210> SEQ ID NO 6
<211> LENGTH: 19
<212> TYPE: DNA
<213> ORGANISM: Homo sapiens

<400> SEQUENCE: 6
tcccaagctg agtttctcc                                                19
```

```
<210> SEQ ID NO 7
<211> LENGTH: 21
<212> TYPE: DNA
<213> ORGANISM: Homo sapiens

<400> SEQUENCE: 7
gacatttact gtgtaggtcg c                                              21

<210> SEQ ID NO 8
<211> LENGTH: 22
<212> TYPE: DNA
<213> ORGANISM: Homo sapiens

<400> SEQUENCE: 8
tggggttggt ttaaaatcct tc                                             22

<210> SEQ ID NO 9
<211> LENGTH: 22
<212> TYPE: DNA
<213> ORGANISM: Homo sapiens

<400> SEQUENCE: 9
cacattataa cctgtgacac cc                                             22

<210> SEQ ID NO 10
<211> LENGTH: 19
<212> TYPE: DNA
<213> ORGANISM: Homo sapiens

<400> SEQUENCE: 10
gtattgctgc ttttggcac                                                 19

<210> SEQ ID NO 11
<211> LENGTH: 21
<212> TYPE: DNA
<213> ORGANISM: Homo sapiens

<400> SEQUENCE: 11
acccaaaaag atgtgagtca c                                              21

<210> SEQ ID NO 12
<211> LENGTH: 21
<212> TYPE: DNA
<213> ORGANISM: Homo sapiens

<400> SEQUENCE: 12
cctttctggt agacgtggaa g                                              21

<210> SEQ ID NO 13
<211> LENGTH: 20
<212> TYPE: DNA
<213> ORGANISM: Homo sapiens

<400> SEQUENCE: 13
cagggtgacc ttccttgtag                                                20

<210> SEQ ID NO 14
<211> LENGTH: 22
<212> TYPE: DNA
<213> ORGANISM: Homo sapiens

<400> SEQUENCE: 14
taagaacgtg tctccagaca cc                                             22
```

```
<210> SEQ ID NO 15
<211> LENGTH: 22
<212> TYPE: DNA
<213> ORGANISM: Homo sapiens

<400> SEQUENCE: 15
agcagatttt ccaagttcca tc                                          22

<210> SEQ ID NO 16
<211> LENGTH: 20
<212> TYPE: DNA
<213> ORGANISM: Homo sapiens

<400> SEQUENCE: 16
agagcaaagg cagacaattg                                             20

<210> SEQ ID NO 17
<211> LENGTH: 21
<212> TYPE: DNA
<213> ORGANISM: Homo sapiens

<400> SEQUENCE: 17
agagatgcaa ctcacctaac c                                           21

<210> SEQ ID NO 18
<211> LENGTH: 21
<212> TYPE: DNA
<213> ORGANISM: Homo sapiens

<400> SEQUENCE: 18
aggtagctgg atcaagagaa c                                           21

<210> SEQ ID NO 19
<211> LENGTH: 22
<212> TYPE: DNA
<213> ORGANISM: Homo sapiens

<400> SEQUENCE: 19
ataccagttg aaactcaaag gg                                          22

<210> SEQ ID NO 20
<211> LENGTH: 19
<212> TYPE: DNA
<213> ORGANISM: Homo sapiens

<400> SEQUENCE: 20
cagtccctac ctttgcaac                                              19

<210> SEQ ID NO 21
<211> LENGTH: 509
<212> TYPE: PRT
<213> ORGANISM: Homo sapiens

<400> SEQUENCE: 21

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60
```

-continued

```
Val Tyr Gln Lys Gly Cys Phe Gln Val Tyr Glu Gln Gly Lys Met Thr
 65                  70                  75                  80

Cys Lys Thr Pro Pro Ser Pro Gly Gln Ala Val Glu Cys Cys Gln Gly
                 85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
        130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala His Gln Ile
        195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480
```

```
Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 22
<211> LENGTH: 509
<212> TYPE: PRT
<213> ORGANISM: Homo sapiens

<400> SEQUENCE: 22

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Glu Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350
```

-continued

```
Ala Asp Leu Gly Leu Ala Val Met His Ser Gln Ser Thr Asn Gln Leu
            355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 23
<211> LENGTH: 509
<212> TYPE: PRT
<213> ORGANISM: Homo sapiens

<400> SEQUENCE: 23

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220
```

```
Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Trp Lys Pro Ala Ile Ala His Arg Asp
            325                 330                 335

Leu Lys Ser Lys Asn Ile Leu Val Lys Lys Asn Gly Gln Cys Cys Ile
        340                 345                 350

Ala Asp Leu Gly Leu Ala Val Met His Ser Gln Ser Thr Asn Gln Leu
    355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
            405                 410                 415

Arg Met Val Ser Asn Gly Ile Val Glu Asp Tyr Lys Pro Pro Phe Tyr
        420                 425                 430

Asp Val Val Pro Asn Asp Pro Ser Phe Glu Asp Met Arg Lys Val Val
    435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
            485                 490                 495

Lys Ile Asp Asn Ser Leu Asp Lys Leu Lys Thr Asp Cys
        500                 505

<210> SEQ ID NO 24
<211> LENGTH: 509
<212> TYPE: PRT
<213> ORGANISM: Homo sapiens

<400> SEQUENCE: 24

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
            85                  90                  95
```

```
Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
        180                 185                 190

Gly Ser Gly Leu Pro Phe Leu Val Gln Arg Thr Val Ala Arg Gln Ile
    195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Glu Lys Pro Ala Ile Ala His Arg Asp
                325                 330                 335

Leu Lys Ser Lys Asn Ile Leu Val Lys Lys Asn Gly Gln Cys Cys Ile
        340                 345                 350

Ala Asp Leu Gly Leu Ala Val Met His Ser Gln Ser Thr Asn Gln Leu
    355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
        420                 425                 430

Asp Val Val Pro Asn Asp Pro Ser Phe Glu Asp Met Arg Lys Val Val
    435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
        500                 505
```

<210> SEQ ID NO 25
<211> LENGTH: 509
<212> TYPE: PRT
<213> ORGANISM: Homo sapiens

<400> SEQUENCE: 25

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Asp Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380
```

```
Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505

<210> SEQ ID NO 26
<211> LENGTH: 509
<212> TYPE: PRT
<213> ORGANISM: Homo sapiens

<400> SEQUENCE: 26

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255
```

```
Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Pro Asn Asp Pro Ser Phe Glu Asp Met Arg Lys Val Val
    435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 27
<211> LENGTH: 508
<212> TYPE: PRT
<213> ORGANISM: Homo sapiens

<400> SEQUENCE: 27

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Gln Val Tyr Glu Gln Gly Lys Met Thr Cys
65                  70                  75                  80

Lys Thr Pro Pro Ser Pro Gly Gln Ala Val Glu Cys Cys Gln Gly Asp
                85                  90                  95

Trp Cys Asn Arg Asn Ile Thr Ala Gln Leu Pro Thr Lys Gly Lys Ser
            100                 105                 110

Phe Pro Gly Thr Gln Asn Phe His Leu Glu Val Gly Leu Ile Ile Leu
        115                 120                 125
```

Ser Val Val Phe Ala Val Cys Leu Leu Ala Cys Leu Leu Gly Val Ala
130                 135                 140

Leu Arg Lys Phe Lys Arg Arg Asn Gln Glu Arg Leu Asn Pro Arg Asp
145                 150                 155                 160

Val Glu Tyr Gly Thr Ile Glu Gly Leu Ile Thr Thr Asn Val Gly Asp
                165                 170                 175

Ser Thr Leu Ala Asp Leu Leu Asp His Ser Cys Thr Ser Gly Ser Gly
            180                 185                 190

Ser Gly Leu Pro Phe Leu Val Gln Arg Thr Val Ala Arg Gln Ile Thr
        195                 200                 205

Leu Leu Glu Cys Val Gly Lys Gly Arg Tyr Gly Glu Val Trp Arg Gly
210                 215                 220

Ser Trp Gln Gly Glu Asn Val Ala Val Lys Ile Phe Ser Ser Arg Asp
225                 230                 235                 240

Glu Lys Ser Trp Phe Arg Glu Thr Glu Leu Tyr Asn Thr Val Met Leu
                245                 250                 255

Arg His Glu Asn Ile Leu Gly Phe Ile Ala Ser Asp Met Thr Ser Arg
            260                 265                 270

His Ser Ser Thr Gln Leu Trp Leu Ile Thr His Tyr His Glu Met Gly
        275                 280                 285

Ser Leu Tyr Asp Tyr Leu Gln Leu Thr Thr Leu Asp Thr Val Ser Cys
290                 295                 300

Leu Arg Ile Val Leu Ser Ile Ala Ser Gly Leu Ala His Leu His Ile
305                 310                 315                 320

Glu Ile Phe Gly Thr Gln Gly Lys Pro Ala Ile Ala His Arg Asp Leu
                325                 330                 335

Lys Ser Lys Asn Ile Leu Val Lys Lys Asn Gly Gln Cys Cys Ile Ala
            340                 345                 350

Asp Leu Gly Leu Ala Val Met His Ser Gln Ser Thr Asn Gln Leu Asp
        355                 360                 365

Val Gly Asn Asn Pro Arg Val Gly Thr Lys Arg Tyr Met Ala Pro Glu
370                 375                 380

Val Leu Asp Glu Thr Ile Gln Val Asp Cys Phe Asp Ser Tyr Lys Arg
385                 390                 395                 400

Val Asp Ile Trp Ala Phe Gly Leu Val Leu Trp Glu Val Ala Arg Arg
                405                 410                 415

Met Val Ser Asn Gly Ile Val Glu Asp Tyr Lys Pro Pro Phe Tyr Asp
            420                 425                 430

Val Val Pro Asn Asp Pro Ser Phe Glu Asp Met Arg Lys Val Val Cys
        435                 440                 445

Val Asp Gln Gln Arg Pro Asn Ile Pro Asn Arg Trp Phe Ser Asp Pro
450                 455                 460

Thr Leu Thr Ser Leu Ala Lys Leu Met Lys Glu Cys Trp Tyr Gln Asn
465                 470                 475                 480

Pro Ser Ala Arg Leu Thr Ala Leu Arg Ile Lys Lys Thr Leu Thr Lys
                485                 490                 495

Ile Asp Asn Ser Leu Asp Lys Leu Lys Thr Asp Cys
            500                 505

<210> SEQ ID NO 28
<211> LENGTH: 509
<212> TYPE: PRT
<213> ORGANISM: Homo sapiens

<400> SEQUENCE: 28

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415
```

```
Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505
```

<210> SEQ ID NO 29
<211> LENGTH: 509
<212> TYPE: PRT
<213> ORGANISM: Homo sapiens

<400> SEQUENCE: 29

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
            35                  40                  45

Glu Gly Gln Gln Cys Phe Ser Ser Leu Ser Ile Asn Asp Gly Phe His
        50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
        130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Glu Ile
            195                 200                 205

Thr Leu Leu Glu Cys Val Gly Lys Gly Arg Tyr Gly Glu Val Trp Arg
        210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
            275                 280                 285
```

Gly Ser Leu Tyr Asp Tyr Leu Gln Leu Thr Thr Leu Asp Thr Val Ser
            290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
            325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
            355                 360                 365

Asp Val Gly Asn Asn Pro Arg Val Gly Thr Lys Arg Tyr Met Ala Pro
            370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
            405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
            485                 490                 495

Lys Ile Asp Asn Ser Leu Asp Lys Leu Lys Thr Asp Cys
            500                 505

<210> SEQ ID NO 30
<211> LENGTH: 509
<212> TYPE: PRT
<213> ORGANISM: Homo sapiens

<400> SEQUENCE: 30

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
            35                  40                  45

Glu Gly Gln Gln Cys Phe Ser Ser Leu Ser Ile Asn Asp Gly Phe His
50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
            85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
            130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
            165                 170                 175

Asp Ser Thr Leu Ala Asp Leu Leu Asp His Ser Cys Thr Ser Gly Ser
        180                 185                 190

Gly Ser Gly Leu Pro Phe Leu Val Gln Arg Thr Val Ala Arg Gln Ile
    195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
            325                 330                 335

Leu Lys Ser Lys Asn Ile Leu Val Lys Lys Asn Gly Gln Cys Cys Ile
        340                 345                 350

Ala Asp Leu Gly Leu Ala Val Met His Ser Gln Ser Thr Asn Gln Leu
    355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
            405                 410                 415

Arg Met Val Ser Asn Gly Ile Val Glu Asp Tyr Lys Pro Pro Phe Tyr
        420                 425                 430

Asp Val Val Pro Asn Asp Pro Ser Phe Glu Asp Met Arg Lys Val Val
    435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
            485                 490                 495

Lys Ile Asp Asn Ser Leu Asp Lys Leu Lys Thr Asp Cys
        500                 505

<210> SEQ ID NO 31
<211> LENGTH: 509
<212> TYPE: PRT
<213> ORGANISM: Homo sapiens

<400> SEQUENCE: 31

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

```
Tyr Met Cys Val Cys Glu Gly Leu Ser Cys Gly Asn Glu Asp His Cys
             35                  40                  45
Glu Gly Gln Gln Cys Phe Ser Ser Leu Ser Ile Asn Asp Gly Phe His
         50                  55                  60
Val Tyr Gln Lys Gly Cys Phe Gln Val Tyr Glu Gln Gly Lys Met Thr
 65                  70                  75                  80
Cys Lys Thr Pro Pro Ser Pro Gly Gln Ala Val Glu Cys Cys Gln Gly
                 85                  90                  95
Asp Trp Cys Asn Arg Asn Ile Thr Ala Gln Leu Pro Thr Lys Gly Lys
                100                 105                 110
Ser Phe Pro Gly Thr Gln Asn Phe His Leu Glu Val Gly Leu Ile Ile
            115                 120                 125
Leu Ser Val Val Phe Ala Val Cys Leu Leu Ala Cys Leu Leu Gly Val
130                 135                 140
Ala Leu Arg Lys Phe Lys Arg Arg Asn Gln Glu Arg Leu Asn Pro Arg
145                 150                 155                 160
Asp Val Glu Tyr Gly Thr Ile Glu Gly Leu Ile Thr Thr Asn Val Gly
                165                 170                 175
Asp Ser Thr Leu Ala Asp Leu Leu Asp His Ser Cys Thr Ser Gly Ser
            180                 185                 190
Gly Ser Gly Leu Pro Phe Leu Val Gln Arg Thr Val Ala Arg Gln Ile
        195                 200                 205
Thr Leu Leu Glu Cys Val Gly Lys Gly Arg Tyr Gly Glu Val Trp Arg
210                 215                 220
Gly Ser Trp Gln Gly Glu Asn Val Ala Val Lys Ile Phe Ser Ser Arg
225                 230                 235                 240
Asp Glu Lys Ser Trp Phe Arg Glu Thr Glu Leu Tyr Asn Thr Val Met
                245                 250                 255
Leu Arg His Glu Asn Ile Leu Gly Phe Ile Ala Ser Asp Met Thr Ser
            260                 265                 270
Arg His Ser Ser Thr Gln Leu Trp Leu Ile Thr His Tyr His Glu Met
        275                 280                 285
Gly Ser Leu Tyr Asp Tyr Leu Gln Leu Thr Thr Leu Asp Thr Val Ser
    290                 295                 300
Cys Leu Arg Ile Val Leu Ser Ile Ala Ser Gly Leu Ala His Leu His
305                 310                 315                 320
Ile Glu Ile Phe Gly Thr Gln Arg Lys Pro Ala Ile Ala His Arg Asp
                325                 330                 335
Leu Lys Ser Lys Asn Ile Leu Val Lys Lys Asn Gly Gln Cys Cys Ile
            340                 345                 350
Ala Asp Leu Gly Leu Ala Val Met His Ser Gln Ser Thr Asn Gln Leu
        355                 360                 365
Asp Val Gly Asn Asn Pro Arg Val Gly Thr Lys Arg Tyr Met Ala Pro
    370                 375                 380
Glu Val Leu Asp Glu Thr Ile Gln Val Asp Cys Phe Asp Ser Tyr Lys
385                 390                 395                 400
Arg Val Asp Ile Trp Ala Phe Gly Leu Val Leu Trp Glu Val Ala Arg
                405                 410                 415
Arg Met Val Ser Asn Gly Ile Val Glu Asp Tyr Lys Pro Pro Phe Tyr
            420                 425                 430
Asp Val Val Pro Asn Asp Pro Ser Phe Glu Asp Met Arg Lys Val Val
        435                 440                 445
```

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505

<210> SEQ ID NO 32
<211> LENGTH: 509
<212> TYPE: PRT
<213> ORGANISM: Homo sapiens

<400> SEQUENCE: 32

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
                20                  25                  30

Tyr Met Cys Val Cys Glu Gly Leu Ser Cys Gly Asn Glu Asp His Cys
            35                  40                  45

Glu Gly Gln Gln Cys Phe Ser Ser Leu Ser Ile Asn Asp Gly Phe His
        50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

```
Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505

<210> SEQ ID NO 33
<211> LENGTH: 7
<212> TYPE: PRT
<213> ORGANISM: Homo sapiens
<220> FEATURE:
<221> NAME/KEY: Variant
<222> LOCATION: (4)..(4)
<223> OTHER INFORMATION: R or H

<400> SEQUENCE: 33

Thr Val Ala Xaa Gln Ile Thr
1               5

<210> SEQ ID NO 34
<211> LENGTH: 21
<212> TYPE: DNA
<213> ORGANISM: Homo sapiens
<220> FEATURE:
<221> NAME/KEY: Variant
<222> LOCATION: (11)..(11)
<223> OTHER INFORMATION: G or A

<400> SEQUENCE: 34
acagtggctc rccagattac a                                           21

<210> SEQ ID NO 35
<211> LENGTH: 7
<212> TYPE: PRT
<213> ORGANISM: Homo sapiens

<400> SEQUENCE: 35

Thr Val Ala Arg Gln Ile Thr
1               5
```

-continued

```
<210> SEQ ID NO 36
<211> LENGTH: 21
<212> TYPE: DNA
<213> ORGANISM: Homo sapiens

<400> SEQUENCE: 36
acagtggctc gccagattac a                                              21

<210> SEQ ID NO 37
<211> LENGTH: 31
<212> TYPE: PRT
<213> ORGANISM: Homo sapiens

<400> SEQUENCE: 37

Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala His Gln Ile
            20                  25                  30

<210> SEQ ID NO 38
<211> LENGTH: 31
<212> TYPE: PRT
<213> ORGANISM: Homo sapiens

<400> SEQUENCE: 38

Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala Arg Gln Ile
            20                  25                  30

<210> SEQ ID NO 39
<211> LENGTH: 31
<212> TYPE: PRT
<213> ORGANISM: Mus musculus

<400> SEQUENCE: 39

Ser Thr Leu Ala Glu Leu Leu Asp His Ser Cys Thr Ser Gly Ser Gly
1               5                   10                  15

Ser Gly Leu Pro Phe Leu Val Gln Arg Thr Val Ala Arg Gln Ile
            20                  25                  30

<210> SEQ ID NO 40
<211> LENGTH: 31
<212> TYPE: PRT
<213> ORGANISM: Xenopus laevis

<400> SEQUENCE: 40

Ser Thr Leu Ala Glu Met Leu Asp His Ser Cys Thr Ser Gly Ser Gly
1               5                   10                  15

Ser Gly Leu Pro Phe Leu Val Gln Arg Thr Val Ala Arg Gln Ile
            20                  25                  30

<210> SEQ ID NO 41
<211> LENGTH: 31
<212> TYPE: PRT
<213> ORGANISM: Danio rerio

<400> SEQUENCE: 41

Ser Thr Leu Ala Asp Leu Met Asp His Ser Cys Thr Ser Gly Ser Gly
1               5                   10                  15

Ser Gly Leu Pro Phe Leu Val Gln Arg Thr Val Ala His Gln Ile
            20                  25                  30
```

<210> SEQ ID NO 42
<211> LENGTH: 35
<212> TYPE: PRT
<213> ORGANISM: Homo sapiens

<400> SEQUENCE: 42

Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala His Gln Ile Thr
            20                  25                  30

Leu Leu Glu
        35

<210> SEQ ID NO 43
<211> LENGTH: 35
<212> TYPE: PRT
<213> ORGANISM: Homo sapiens

<400> SEQUENCE: 43

Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala Arg Gln Ile Thr
            20                  25                  30

Leu Leu Glu
        35

<210> SEQ ID NO 44
<211> LENGTH: 35
<212> TYPE: PRT
<213> ORGANISM: Homo sapiens

<400> SEQUENCE: 44

Lys Thr Leu Gln Asp Leu Val Tyr Asp Leu Ser Thr Ser Gly Ser Gly
1               5                   10                  15

Ser Gly Leu Pro Leu Phe Val Gln Arg Thr Val Ala Arg Thr Ile Val
            20                  25                  30

Leu Gln Glu
        35

<210> SEQ ID NO 45
<211> LENGTH: 35
<212> TYPE: PRT
<213> ORGANISM: Homo sapiens

<400> SEQUENCE: 45

Lys Thr Leu Lys Asp Leu Ile Tyr Asp Val Thr Ala Ser Gly Ser Gly
1               5                   10                  15

Ser Gly Leu Pro Leu Leu Val Gln Arg Thr Ile Ala Arg Thr Ile Val
            20                  25                  30

Leu Gln Glu
        35

<210> SEQ ID NO 46
<211> LENGTH: 35
<212> TYPE: PRT
<213> ORGANISM: Homo sapiens

```
<400> SEQUENCE: 46

Thr Met Leu Gly Asp Leu Leu Asp Ser Asp Cys Thr Thr Ser Gly
1               5                   10                  15

Ser Gly Leu Pro Phe Leu Val Gln Arg Thr Val Ala Arg Gln Val Ala
                20                  25                  30

Leu Val Glu
        35

<210> SEQ ID NO 47
<211> LENGTH: 35
<212> TYPE: PRT
<213> ORGANISM: Homo sapiens

<400> SEQUENCE: 47

Glu Ser Leu Lys Asp Leu Ile Asp Gln Ser Gln Ser Ser Gly Ser Gly
1               5                   10                  15

Ser Gly Leu Pro Leu Leu Val Gln Arg Thr Ile Ala Lys Gln Ile Gln
                20                  25                  30

Met Val Arg
        35

<210> SEQ ID NO 48
<211> LENGTH: 35
<212> TYPE: PRT
<213> ORGANISM: Homo sapiens

<400> SEQUENCE: 48

Glu Ser Leu Arg Asp Leu Ile Glu Gln Ser Gln Ser Ser Gly Ser Gly
1               5                   10                  15

Ser Gly Leu Pro Leu Leu Val Gln Arg Thr Ile Ala Lys Gln Ile Gln
                20                  25                  30

Met Val Lys
        35

<210> SEQ ID NO 49
<211> LENGTH: 19
<212> TYPE: PRT
<213> ORGANISM: Homo sapiens

<400> SEQUENCE: 49

Thr Gly Leu Pro Leu Leu Val Gln Arg Thr Ile Ala Arg Thr Ile Val
1               5                   10                  15

Leu Gln Glu
```